(12) United States Patent
Apte et al.

(10) Patent No.: US 10,415,105 B2
(45) Date of Patent: *Sep. 17, 2019

(54) METHOD AND SYSTEM FOR DIAGNOSTIC TESTING

(71) Applicant: uBiome, Inc., San Francisco, CA (US)

(72) Inventors: Zachary Apte, San Francisco, CA (US); Jessica Richman, San Francisco, CA (US); Daniel Almonacid, San Francisco, CA (US)

(73) Assignee: uBiome, Inc., San Francisco, CA (US)

( * ) Notice: Subject to any disclaimer, the term of this patent is extended or adjusted under 35 U.S.C. 154(b) by 246 days.

This patent is subject to a terminal disclaimer.

(21) Appl. No.: 15/198,818

(22) Filed: Jun. 30, 2016

(65) Prior Publication Data

US 2017/0002432 A1  Jan. 5, 2017

Related U.S. Application Data

(60) Provisional application No. 62/186,793, filed on Jun. 30, 2015.

(51) Int. Cl.
| | | |
|---|---|---|
| *G01N 33/48* | (2006.01) |
| *C12Q 1/70* | (2006.01) |
| *A61B 10/00* | (2006.01) |
| *C12Q 1/689* | (2018.01) |
| *G06G 7/58* | (2006.01) |

(52) U.S. Cl.
CPC .......... *C12Q 1/708* (2013.01); *A61B 10/0096* (2013.01); *C12Q 1/689* (2013.01)

(58) Field of Classification Search
None
See application file for complete search history.

(56) References Cited

U.S. PATENT DOCUMENTS

| | | | |
|---|---|---|---|
| 5,891,630 | A | 4/1999 | Eggers et al. |
| 8,478,544 | B2 | 7/2013 | Colwell et al. |
| 9,710,606 | B2 | 7/2017 | Apte et al. |
| 2002/0146745 | A1 | 10/2002 | Natan et al. |
| 2005/0255552 | A1 | 11/2005 | Flynn et al. |
| 2006/0246423 | A1 | 11/2006 | Adelson et al. |
| 2007/0259337 | A1 | 11/2007 | Hully et al. |
| 2008/0299567 | A1 | 12/2008 | Marshall et al. |
| 2010/0129816 | A1 | 5/2010 | Savelkoul et al. |
| 2010/0143305 | A1 | 6/2010 | Lemke |
| 2010/0172874 | A1 | 7/2010 | Turnbaugh et al. |
| 2012/0045771 | A1 | 2/2012 | Beier et al. |
| 2012/0149584 | A1 | 6/2012 | Olle et al. |
| 2013/0045874 | A1 | 2/2013 | Ehrlich |
| 2013/0316922 | A1 | 11/2013 | Balashov et al. |
| 2014/0093478 | A1 | 4/2014 | Turnbaugh et al. |
| 2014/0136120 | A1 | 5/2014 | Colwell et al. |
| 2014/0179726 | A1 | 6/2014 | Bajaj et al. |
| 2014/0199281 | A1 | 7/2014 | Henn et al. |
| 2015/0054930 | A1 | 2/2015 | Bangera et al. |
| 2015/0111788 | A1 | 4/2015 | Fernandez et al. |
| 2015/0133391 | A1 | 5/2015 | De Vlaminick et al. |
| 2015/0213193 | A1 | 7/2015 | Apte et al. |
| 2016/0110515 | A1 | 4/2016 | Apte et al. |
| 2016/0232312 | A1 | 8/2016 | Apte et al. |
| 2016/0362738 | A1 | 12/2016 | Apte et al. |

FOREIGN PATENT DOCUMENTS

| | | |
|---|---|---|
| WO | 2010/126375 A1 | 11/2010 |
| WO | 2014144092 A1 | 9/2014 |
| WO | 2014/165810 A2 | 10/2014 |
| WO | 2015067936 A1 | 5/2015 |

OTHER PUBLICATIONS

Cole et al. The Ribosomal Database Project: improved alignments and new tools for rRNA analysis. Nucl Acids Res Jan. 2009 vol. 37 pp. D141-D145. Especially p. 141 col. 1 paral, D143 col. 1 para3.
Darmanis et al. ProteinSeq: high-performance proteomic analyses by proximity ligation and next generation sequencing. PLos One Sep. 29, 2011 vol. 6 No. 9 pp. e25583 pp. 1-10. Especially abstract, p. 2 col. 1 para 4-6, p. 3 fig 1, p. 4 col. 2 para2, p. 6 fig 3c, p. 7 col. 1 para2, p. 7 col. 2, p. 8 col. 2 para 6-7.
IDT Decoded Newsletter. Improving Immuno-PCR by Optimizing Antibody-Oligo Conjugation. [online] Mar. 11, 2015 [retrieved Aug. 29, 2016]. Available on the internet:<URL: https://www.idtdna.com/pages/decoded/decoded-articles/your-research/decoded/2015/03/11/improving-immuno-pcr-by-optimizing-antibody-oligo-conjugation>. Especially PDF p. 2 para 3, PDF p. 3 para 2, PDF p. 3 fig 1, PDF p. 6 para5, PDF p. 7 para 1.
Mahmood et al. Western Blot: technique, theory, and trouble shooting. N Am J Med Sci Sep. 2012 vol. 4 No. 9 p. 429-434. Especially p. 3.
U.S. Appl. No. 16/047,840, Title—Disease-Associated Microbiome Characterization Process, mailed on Jul. 27, 2018.
International Application No. PCT/US2016/040411, International Preliminary Report on Patentability dated Jan. 11, 2018, 12 pages.
International Application No. PCT/US2016/040411, International Search Report and Written Opinion dated Nov. 2, 2016, 14 pages.

(Continued)

*Primary Examiner* — Eric S Dejong
(74) *Attorney, Agent, or Firm* — Kilpatrick, Townsend & Stockton LLP

(57) ABSTRACT

An embodiment of a method for diagnostic testing includes: providing a sampling kit to a subject, the sampling kit including a sample container for reception of a sample from a collection site of the subject; receiving the sample from the subject; generating a microbiome sequence dataset based upon sequencing nucleic acid content of a microorganism portion of the sample; detecting a presence of a set of microbiome targets; generating a diagnostic analysis based on the detected set of microbiome targets; generating a therapy recommendation based on the set of microbiome targets; and promoting the therapy recommendation in coordination with presenting information derived from the diagnostic analysis.

9 Claims, 9 Drawing Sheets

(56) References Cited

OTHER PUBLICATIONS

Extended European Search Report and Opinion from European Appln. 16818792.0; dated Nov. 19, 2018; 11 pages.
Brotman, R.M. et al.; "Interplay Between the Temporal Dynamics of the Vaginal Microbiota and Human Papillomavirus Detection"; *Journal of Infectious Diseases*; vol. 210, No. 11; Jun. 18, 2014; pp. 1723-1733.
Lee, T.; "Swabbing for Science"; *Berkeley Science Review*. Apr. 22, 2013; 14 pages.
Nardis, C. et al.; "Vaginal microbiota and viral sexually transmitted diseases"; *Ann. Ig.*; vol. 25; Sep. 1, 2013; pp. 443-456.
"OraRisk HPV"; Oral DNA Labs; 2013; retrieved from the internet http://www.oraldna.com/Resources/OraRiskHPVCutSheet.pdf; 2 pages.
"PCR Technologies: A Technical Guide"; *Sigma-Aldrich*; Dec. 31, 2014; retrieved from the internet https://www.sigmaaldrich.com/content/dam/sigma-aldrich/docs/Sigma-Aldrich/General_Information/1/pcr-technoogies-guide.pdf; 164 pages.
Weinstock, G.M.; "Genomic approaches to studying the human microbiota"; Nature; vol. 489, No. 7415; Sep. 1, 2012; pp. 250-256.
Wylie, K.M. et al.; "Metagenomic analysis of double-stranded DNA viruses in healthy adults"; *BMC Biology*; Biomed Central, London, GB; vol. 12, No. 1; Sep. 10, 2014; pp. 71-80.

Actual Sequence of S1 and S2 unknown based upon sequencing of fragments:
A....C or A....G for S1?
T....C or T....G for S2?

- Determine distribution of A, C, T, and G at each position
- Determine entropy at each position
- Form clusters based on entropy
- Determine actual sequence

METHOD AND SYSTEM FOR DIAGNOSTIC TESTING

CROSS-REFERENCE TO RELATED APPLICATIONS

This application claims the benefit of U.S. Provisional Application Ser. No. 62/186,793 filed 30 Jun. 2015, which is hereby incorporated in its entirety by this reference.

TECHNICAL FIELD

This invention relates generally to the field of immunology and microbiology and more specifically to a new and useful method and system for diagnostic testing in the field of immunology and microbiology.

BACKGROUND

Diagnostic testing is used to provide insight into the health status of a subject, and, when performed in a timely manner can facilitate identification of proper treatment methods for positively diagnosed subjects. Current methods of diagnostic testing are, however, time consuming, labor intensive, and can be prohibitively expensive to implement. Furthermore, current tests for different disease panels typically include a very limited number of tests (e.g., ~10 tests), do not provide results in a rapid manner, and are prescribed after consultation with a doctor, which can discourage some subjects from undergoing diagnostic testing due to operational inefficiencies, patient sensitivity (e.g., in relation to fear of results, in relation to feelings of shame, etc.) and other factors.

As such, there is a need in the field of immunology and microbiology for a new and useful method and system for diagnostic testing. This invention creates such a new and useful method and system.

DESCRIPTION OF THE EMBODIMENTS

The following description of the embodiments of the invention is not intended to limit the invention to these embodiments, but rather to enable any person skilled in the art to make and use this invention.

1. Overview.

Figure 1A:
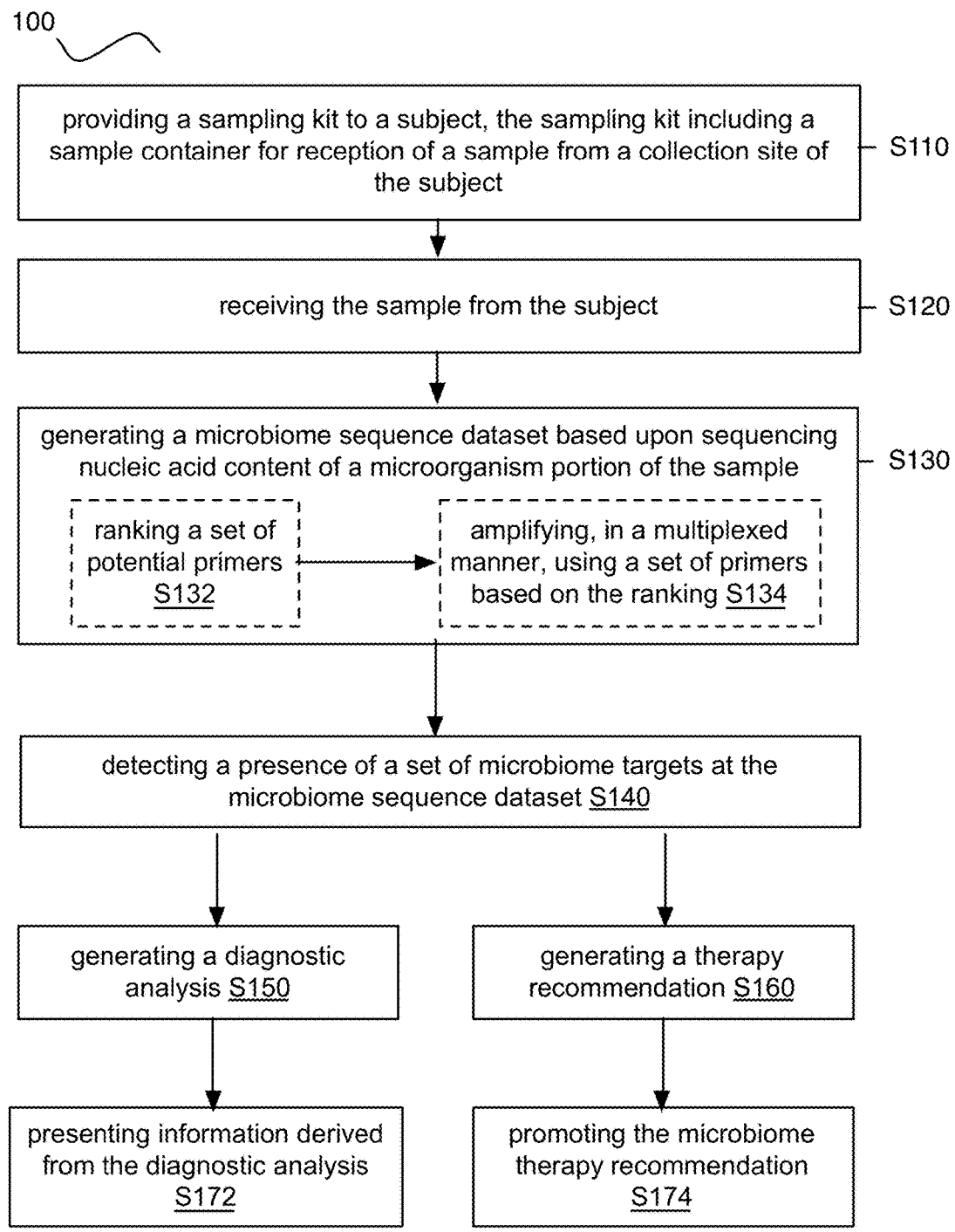
FIGS. 1A-1C are a schematics of an embodiment of a method and system for diagnostic testing.
Figure 1B:
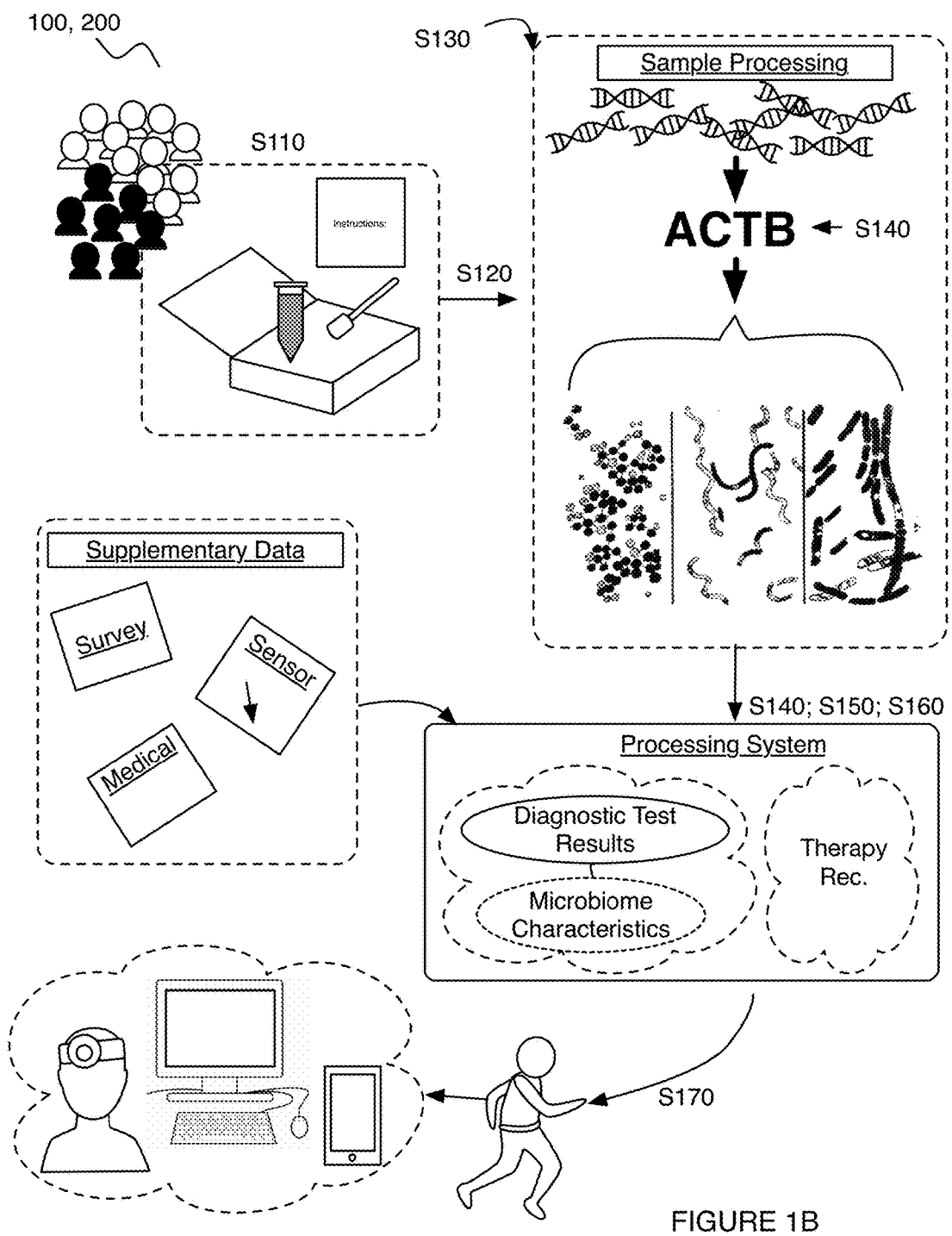
Figure 1C:
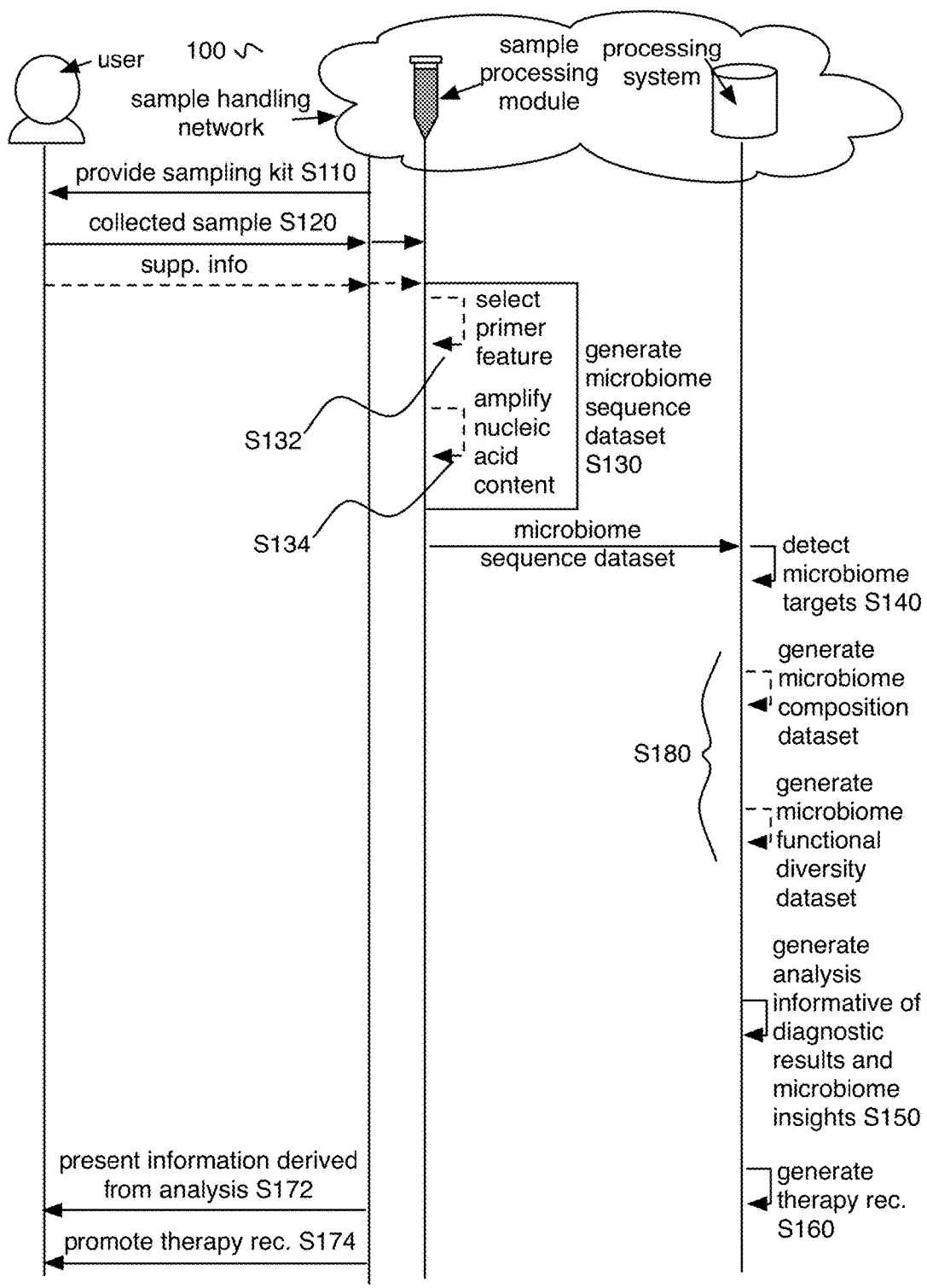

As shown in FIGS. 1A-1C, an embodiment of a method 100 for diagnostic testing includes: providing a sampling kit to a subject, the sampling kit including a sample container for reception of a sample from a collection site of the subject S110; receiving the sample from the subject S120; generating a microbiome composition dataset based upon sequencing nucleic acid content of a microorganism portion of the sample S130; detecting a presence of at least one of a set of microbiome targets and a set of targets associated with sexually transmitted diseases (STDs) S140; generating a microbiome functional diversity dataset S145; generating a diagnostic analysis based on the detected set of microbiome targets, wherein the diagnostic analysis is informative of microbiome aspects of the sample and assessment of STD presence associated with the sample S150; generating a therapy recommendation based on the set of microbiome targets S160; and promoting the therapy recommendation in coordination with presenting information derived from the diagnostic analysis S170.

The method 100 functions to comprehensively test a sample for presence of markers of a set of diseases in parallel and to additionally generate analyses indicative of characteristics of the microbiome of the sample site of the user. As such, the method 100 can simultaneously or otherwise contemporaneously test a single sample from a subject for multiple disease markers and/or microbiome characteristics in a multiplex manner, thereby providing health-state insights to the user beyond the insights of currently available diagnostic tests. In some variations, the method 100 can further generate insights in relation to correlations/associations between different disease states and microbiome characteristics from one or more sample sites of the subject, thereby linking microbiome dynamics to certain disease states of a subject. As such, the method 100 can perform testing for detection of one or more of: viruses, prokaryotic organisms, eukaryotic organisms (including fungal organisms), bacteria, any other suitable organism, any other suitable product of an organism (e.g., genetic material), any other suitable portion of an organism, and/or any other suitable marker.

In a specific application, the method 100 can diagnose and/or provide information regarding STDs including: viral infections (e.g., human papillomavirus, genital herpes, hepatitis B virus, human immunodeficiency virus, etc.), bacterial infections (e.g., *chlamydia*, gonorrhea, syphilis, etc.), parasitic infections (e.g., trichomoniasis, pubic lice, scabies, etc.), fungal infections (e.g., yeast infection, etc.). For example, the method 100 can be used to comprehensively test a sample from a human subject for presence of markers associated with sexually transmitted diseases, while simultaneously characterizing the microbiota of the genital region(s) (or other regions) of the subject. In more detail, the specific application of the method 100 can simultaneously/contemporaneously test a sample for viruses including: high risk and other Papillomavirus types (e.g., Human papillomavirus types 1a, 2, 2a, 3, 4, 5, 5b, 6, 6a, 6b, 7, 8, 9, 10, 11, 12, 13, 14D, 15, 16, 17, 18, 19, 20, 21, 22, 23, 24, 25, 26, 27, 27b, 28, 29, 30, 31, 32, 33, 34, 35, 36, 37, 38, 38b, 39, 40, 41, 43, 44, 45, 47, 48, 49, 50, 51, 52, 53, 55, 56, 57, 57b, 57c, 58, 59, 60, 61, 62, 63, 65, 66, 67, 68, 68a, 68b, 69, 70, 71, 72b, 78, 81, 82, 83, 84, 86, 87, 88, 90, 94, 97, 98, 99, 100, 101, 102, 103, 104, 105, 106, 107, 108, 109, 110, 111, 112, 113, 114, 115, 117, 118, 119, 120, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 154, 155, 156, 159, 163, 171, 172, 173 and 197), Herpes simplex virus (Herpes simplex virus types 1 and 2), and human immunodeficiency virus (HIV, types I and II).

The specific application of the method 100 can additionally, simultaneously and/or contemporaneously test a sample for condition-associated prokaryotic organisms including:

*Haemophilus ducreyi* (associated with Chancroid), *Chlamydia trachomatis* (associated with *Chlamydia*), *Neisseria gonorrhoeae* (associated with Gonorrhea), *Mycoplasma genitalium* (associated with *Mycoplasma*), *Gardnerella vaginalis* (associated with Vaginitis), *Treponema pallidum* (associated with Syphilis), and any other suitable prokaryotic organism (e.g., detectable through 16S rRNA metagenomic sequencing), provoking other conditions such as pelvic inflammatory disease (PID) or another sign of illness. The specific application of the method 100 can additionally, simultaneously and/or contemporaneously test a sample for condition-associated eukaryotic organisms including *Trichomonas vaginalis* (associated with Trichomoniasis) and any other suitable eukaryotic organism (e.g., detectable through 18S rRNA metagenomic sequencing). However, variations of the specific application of the method 100 can additionally or alternatively be used to provide diagnostics associated with any other suitable disease(s) and/or characterize the microbiome of any other sample site(s).

The method 100 is preferably implemented at least in part at a system 200, as shown in FIG. 1B, including a sample handling network (e.g., with sample kit distribution and sample reception modules); a sample processing module, in communication with the sample handling network, that amplifies targets of received samples and generates sequence datasets associated with targets of the samples; and a computing system configured to generate and provide analyses derived from processing of the samples, in support of diagnostic tests of the received samples. At least a portion of the method 100 can be implemented according to the systems and methods described in U.S. application Ser. No. 14/593,424 entitled "Method and System for Microbiome Analysis" and filed on 9 Jan. 2015, which is herein incorporated in its entirety by this reference. However, the method 100 can additionally or alternatively be implemented using any other suitable system(s).

2. Benefits.

In specific examples, the method 100 and/or system 200 can confer several benefits over conventional methodologies for analyzing a microbiome of an individual in order to, for example, diagnose a sexually-transmitted disease (STD) or characterize a panel of STDs in an assessment, along with providing generalized characterizations of the microbiome of a subject (e.g., in terms of composition and functional aspects), in promoting health of the subject. Conventional methodologies can be inefficient, inconvenient, low throughput, low specificity, and/or possess other unsuitable characteristics for microbiome analysis. However, in specific examples, the method 100 and/or system 200 can perform one or more of the following:

First, the technology can analyze a microbiome (and/or a human genome) of an individual in a multiplex manner, thereby facilitating a high throughput, comprehensive, specific diagnostic test for a plurality of sexually transmitted infections, and/or for a plurality of types of a given sexually transmitted infection (e.g., a diagnostic test for multiple types of HPV). For example, the technology can analyze for the presence of a panel of STDs on the order of at least 100's or 1000's of STDs. Additionally or alternatively, a sample used in performing the diagnostic test can be contemporaneously analyzed for determining insights about microbiome, and used to provide generalized characterizations of the microbiome of a subject (e.g., in terms of composition and functional aspects). For example, primers can be algorithmically selected in relation to the amplification process for compatibility with a specific set of targets from which both diagnostic results and general microbiome insights can be generated. Thus, the technology can perform a comprehensive microbiome analysis to infer a variety of health indicators for an individual, thereby improving efficiency and the overall benefit extracted out of a given collected sample.

Second, the technology can enable a user to collect a single sample (e.g., at home, at work, remote from a health care provider, when the user is mobile, when the user is stationary, at any time of the day, etc.), and subsequently be digitally informed of both diagnostic results regarding a disease or a panel of diseases (e.g., an STD panel) as well as insights about their microbiome (e.g., health, composition, functionality, correlations with behavioral and/or demographic characteristics, etc.). Additionally or alternatively, the sampling kit can facilitate a third party (e.g., a guardian, a care provider) and/or any suitable entity to collect a sample from the user. As such, the technology can be tailored for an optimal user experience through improvement of time investment, adherence, education, and treatment outcomes over conventional methodologies.

Third, the technology can generate and promote a therapy recommendation personalized for an individual based on their microbiome. Such therapy recommendations can include microbiome modification therapies (e.g., dietary supplementation with prebiotics/probiotics, physical activity recommendations, etc.), healthcare provider-related recommendations (e.g., suggestions to see a healthcare provider, facilitation of communication between user and physician), and/or any suitable (invasive or non-invasive) therapy recommendation tailored to an individual's microbiome make-up and situation, as further described below.

Fourth, a therapy recommendation and/or information derived from a microbiome can be accessible over any suitable device of the user (e.g., through a web portal associated with a user account, through a mobile application, etc.), thus enabling a seamless user experience from the beginning of the sample collection process to receiving the results inferred from the collected sample. Additionally or alternatively, the method 100 and/or system 200 can automatically implement a portion of the therapy recommendation (e.g., facilitating telemedicine, placing a probiotic supplementation order, notifying a health provider, etc.).

The technology can, however, provide any other suitable benefit(s) in the context of microbiome analysis in the context of a disease, a panel of diseases (e.g., an STD panel), or any other suitable health-related state.

3. Method

As shown in FIGS. 1A-1C, an embodiment of a method 100 for diagnostic testing includes: providing a sampling kit to a subject, the sampling kit including a sample container for reception of a sample from a collection site of the subject S110; receiving the sample from the subject S120; generating a microbiome sequence dataset based upon sequencing nucleic acid content of a microorganism portion of the sample S130; detecting a presence of at least one of a set of microbiome targets and a set of targets associated with sexually transmitted diseases (STDs) S140; generating a microbiome functional diversity dataset S145; generating a diagnostic analysis based on the detected set of microbiome targets, wherein the diagnostic analysis is informative of microbiome aspects of the sample and assessment of STD presence associated with the sample S150; generating a therapy recommendation based on the set of microbiome targets S160; and promoting the therapy recommendation in coordination with presenting information derived from the diagnostic analysis S170.

3.1 Providing a Sampling Kit.

As shown in FIGS. 1A-1C, Block S110 recites: providing a sampling kit to a subject, the sampling kit including a sample container for reception of a sample from a collection site of the subject, which functions to provide a kit to the subject, whereby the subject can perform a self-sampling activity in delivering the sample to a sample handling network associated with Block S120. The sampling kit preferably includes instructions for use, a sample kit identifier, a sample-receiving substrate (e.g., container, permeable substrate, etc.) with an associated identifier, and an apparatus (e.g., swab, lancet, etc.) by which the subject can collect the sample from the collection site. The sample-receiving substrate of the sampling kit can, in some variations, be provided with a sample processing reagent (e.g., lysis reagent, etc.) or pre-processing reagent (e.g., sample preservation reagent, etc.), which, with the instructions, can be used by the subject to transition the sample to a pre-processed or processed state prior to reception at the sample handling network. Additionally or alternatively, the sampling kit can be configured to automatically process a sample collected by a user (e.g., a sampling kit includes a processing chamber into which a user places a sample, where the processing chamber is configured to automatically process the sample in response to receipt of the sample.).

In one example of a sampling kit provided in Block S110, the sample-receiving substrate can include a vial with a cap for reception of a sample from a collection site of the subject. In another example, the sample-receiving substrate can include a permeable membrane for reception of a blood sample (e.g., drop of blood) from the subject. However, the sample-receiving substrate can additionally or alternatively include any other suitable substrate. The sampling kit can include one or more elements of the sampling kit described in U.S. application Ser. No. 14/593,424 entitled "Method and System for Microbiome Analysis" and filed on 9 Jan. 2015. However, the sampling kit can additionally or alternatively include any other suitable elements.

In Block S110, the collection site can be associated with one or more of: the female genitals, the male genitals, the rectum, the gut, the skin, the mouth, the nose, any mucous membrane, and any other suitable sample providing site (e.g., blood, sweat, urine, feces, semen, vaginal discharges, tears, tissue samples, interstitial fluid, other body fluid, etc.) of the subject. In a specific example with regard to the female genitals, instructions for sample provision can include wetting a swab provided in the sampling kit with polymerase chain reaction (PCR) water provided in the sampling kit, and wiping the wetted swab in the area just inside the vaginal opening, to the depth of cotton on the swab, for one minute (e.g., with spreading of the labia using the hand not performing the swabbing motion). In another specific example with regard to the male genitals, instructions for sample provision include wetting a swab provided in the sampling kit with polymerase chain reaction (PCR) water provided in the sampling kit, and wiping the wetted swab in a circular motion around the base of the head of the penis for one minute (e.g., with pulling back of the foreskin, if necessary). In another specific example with regard to a blood sample, instructions for sample provision include pricking the finger, and allowing a drop of blood to contact a fibrous card for downstream processing of a dried blood spot. The sampling kit is preferably configured to facilitate user collection of the sample in a non-invasive manner. However, the collection site/instructions for sample provision can be configured in any other suitable manner.

With respect to Block S110, providing a sampling kit can be performed in response to a purchasing order by a user (e.g., through an application executing on a user device, website, mail order, in-person order, and/or through any suitable purchasing means), by a care provider, and/or by any suitable entity. However, a sampling kit can be provided in response to any suitable action by any suitable entity. Components of a sampling kit preferably do not expire or otherwise have a significantly long shelf life, such that a sampling kit can be used to validly collect and receive a sample from a user at any time point after the sampling kit is provided to the user. Additionally or alternatively, sampling kit components can be reusable, disposable, and/or have any suitable usability characteristic. In a specific example, processing reagents of a sampling kit can be applied to multiple samples collected by a user (e.g., such that a user does not need to repurchase certain components of a sampling kit for different microbiome tests). However, different components of the sampling kit can have any suitable lifespan.

Providing the sampling kit in Block S110 is can be implemented through an appropriate care provider (e.g., health diagnostic center, pharmacy, medical practitioner, etc.). Providing the sampling kit in Block S110 can alternatively be performed in a manner that requires little effort from the subject (e.g., in variations wherein the subject is a human subject). In particular, provision of the sampling kit in Block S110 is preferably performed in a manner that does not require a doctor's visit or significant consultation in order to receive the sampling kit for diagnostic testing. In variations, the sampling kit can be provided to a subject upon request by the subject (e.g., using an online ordering system, by ordering through a healthcare provider, upon purchase at a pharmacy, etc.), or can alternatively be provided to the subject upon request by a healthcare provider or other caretaker (e.g., significant other, relative, friend, acquaintance, etc.) associated with the user. In particular, to facilitate convenience in reception of the sampling kit by a subject, a subject can order the sampling kit upon completion of a survey that fulfills screening requirements for diagnostic testing, without requiring the user to directly interface with a healthcare provider. In a specific example, Block S110 can include from a sample handling network, providing a sampling kit to the individual at a location remote from the sample processing network, the sampling kit including a sample container configured to receive a sample from a collection site of the individual. However, a sampling kit can be provided to a user at any suitable location in any suitable manner.

In a specific example of Block S110 associated with testing of a panel of sexually transmitted diseases (STDs), a subject can order a sampling kit through an electronic (e.g., online) ordering system, whereby the subject completes an initial screening survey that asks for age information and sexual activity status (e.g., "are you sexually active?"). Upon completion of the survey, the subject can then be directed to provide information required for completion of the order (e.g., delivery address, payment information, insurance information, etc.), after which the sampling kit is delivered to the subject (e.g., by way of a parcel delivery service, by way of a courier service, by way of a mailing service, etc.). In another example, a subject can order a sampling kit through a pharmacy or drugstore, whereby the subject completes an initial screening survey that asks a limited amount of required information. Upon completion of the survey, the subject can then purchase the sampling kit for use. As such, in these and similar examples, the subject can receive the sampling kit for diagnostic testing, with little effort or embarrassment.

Regarding Block S110, some variations of the method 100 can, however, include provision of the sampling kit to a subject in any other suitable manner. Still alternative variations of the method 100 can entirely omit providing a sampling kit to the subject for self-sampling of a collection site by the subject in Block S110, and can instead include reception of a sample from the subject in any other suitable manner.

3.2 Receiving a Sample.

As shown in FIGS. 1A-1C, Block S120 recites: receiving the sample from the subject, which functions to enable sample processing and generation of data that can be used to provide diagnostic test results. As noted above, reception of sample-receiving substrates in Block S120 can be facilitated using one or more of a parcel delivery service and a courier service, or can alternatively be directly enabled with delivery of a sample container to the sample handling network by the subject associated with the sample-receiving substrate. However, Block S120 can alternatively include receiving the sample from the subject using any other suitable sample handling network-sample delivery service relationship. Furthermore, samples received in Block S120 can be in a pre-processed or processed state (e.g., a state of lysing due to agitation of a sample by an individual in Block S110, through components of the sampling kit facilitating automatic processing of the sample, etc.), or can alternatively be in any other suitable state upon reception at the sample handling network. However, the sample can be received at any suitable location, and/or the sample can be completely processed by the subject (e.g., the subject collecting the sample at a collection site of the subject) at a location associated with the subject (e.g., at home).

With respect to Block S120, the received sample preferably includes microorganism genetic material (e.g., microorganism DNA, microorganism RNA, etc.). In specific examples, one or more collected samples can include genetic and/or other suitable biological material from viruses, prokaryotic microorganisms, eukaryotic microorganisms (including fungal organisms), bacteria and/or any other suitable microorganism. Additionally or alternatively, the sample can contain human genetic material (e.g., DNA of the human user), animal genetic material (e.g., DNA of a pet), and/or non-living matter, each of which can be analyzed (e.g., for disease markers) in addition to or as an alternative to analysis of the microorganism material. In a specific example, the sample can include a microorganism portion comprising a plurality of microorganism types associated with the plurality of STDs. In the specific example, the plurality of microorganism types can comprise viral microorganisms and non-viral organisms, and wherein the plurality of STDs can comprise a viral STD and a non-viral STD. However, the received sample can include any suitable material As indicated above, in variations of the method 100 that omit self-sampling by the subject in Block S110, Block S120 can include reception of a sample in a manner alternative to that described above. In one such alternative variation, reception of a sample and/or a sample-receiving substrate in Block S120 can be facilitated using a laboratory-based or a clinical-based intermediary that has staff trained in sample extraction from a subject and transmission of extracted samples to the sample handling network. As such, the subject in this alternative variation provides a sample from a collection site, and sample handling and delivery is performed without involvement of the subject. However, reception of the sample at the sample handling network can be implemented in Block S120 in any other suitable manner.

In a variation of Block S120, processing and analysis (e.g., as in Blocks S130, S140, S150, S160) of a collected sample can be performed by the user, such that the user can receive a diagnostic analysis and/or a therapy recommendation (e.g., as in Block S170) without sending the sample to a remote sample handling network. In this variation, receiving the sample can include receiving the sample at a processing compartment of a sampling kit, the processing compartment configured to facilitate generation of a microbiome sequence dataset from the collected sample. Additionally or alternatively, in this variation, the sampling kit can include instructions and/or requisite processing reagents for a user to perform processing on a collected sample. However, Block S120 and/or any suitable portion of the method 100 can be performed at a sample handling network, by a user, by a third party, and/or by any suitable entity.

3.3 Generating a Microbiome Composition Dataset.

As shown in FIGS. 1A-1C, Block S130 recites: generating a microbiome sequence dataset based upon sequencing nucleic acid content of a microorganism portion of the sample S130, which functions to sequence nucleic acid content corresponding to a collected sample's microorganism portion in generating data that can be used to provide comprehensive diagnostic results from the sample. Generating a microbiome sequence S130 can additionally or alternatively include: ranking a set of candidate primers S132, contemporaneously amplifying present targets of a set of targets from the sample with a processing device and a set of compatible primers S134, and/or controlling fragment size selection for amplification.

With respect to Block S130, generating a microbiome sequence dataset is preferably performed at a sample handling network (e.g., at a sample processing module of a sample handling network). Different portions of Block S130 (e.g., Block S132, S134, etc.) can be performed at different portions of the sample handling network, and/or at different locations other than the sampling handling network. However, Block S130 can be performed by or at any suitable entity. A generated microbiome sequence dataset preferably includes sequenced nucleic acid material of a microorganism portion of a collected sample, but can additionally or alternatively include sequenced nucleic acid material of any other portion of the sample (e.g., non-microbiome portions of the sample), microbiome composition characteristics (e.g., types of microbiota, amounts of microbiota, proportion of microbiota, microbiota composition properties in relation to other physiological properties, etc.), and/or include any other suitable data for subsequent diagnostic analysis and/or generation of a therapy recommendation.

Regarding Block S130, generating a microbiome sequence dataset preferably includes generating a microbiome sequence dataset corresponding to nucleic acid content from a microorganism portion of the sample. Additionally or alternatively, a microbiome sequence dataset can be generated using a human portion of the sample (e.g., DNA of the user, DNA of a third party, etc.), an animal portion of the sample (e.g., DNA of a pet, etc.), and/or any suitable portion of the sample. In an example, Block S130 can include, at a sample processing module within the sample handling network, generating a microbiome sequence dataset based upon sequencing nucleic acid content of a microorganism portion of the sample. In another example, Block S130 can include, at a sample processing module, generating a microbiome sequence dataset based upon sequencing nucleic acid content of a microorganism portion of the sample, the microorganism portion comprising a plurality of microorganism types associated with the plurality of STDs. In this example, microorganism portion can include papillomavirus microorganisms (i.e., related to HPV) and bacterial microorganisms, wherein generating the microbiome sequence dataset comprises generating the microbiome sequence dataset based upon sequencing nucleic acid content of the papillomavirus microorganisms and the bacterial microorganisms. Generating the microbiome sequence dataset is preferably performed using selected features of primers and/or targets (e.g., selected as in Block S132), and amplicons generated from microorganism nucleic acid content in the sample and primers corresponding to the selected primer and/or target features. For example, generating a microbiome sequence dataset can include pre-processing a collected sample or portion of the collected sample (e.g., lysing the collected sample to expose nucleic acid content of a microorganism portion of the sample); amplifying the nucleic acid content using a set of primers and/or a processing protocol identified based on desired target and/or primer features (e.g., as in Block S132); and generating a microbiome sequence dataset from sequencing amplicons generated from amplifying the nucleic acid content. Additionally or alternatively, generating the microbiome sequence dataset can include generating the microbiome sequence dataset with processes adapted to specific fragment size preferences (e.g., in relation to using a Nextera kit), supplementary data (e.g., survey response information, supplemental sensor information, user demographic information, etc.), and/or any other suitable data or sample feature.

In variations, generating a microbiome sequence dataset as in Block S130 can implement techniques including one or more of: sequencing-by-synthesis techniques (e.g., Illumina sequencing), capillary sequencing techniques (e.g., Sanger sequencing), pyrosequencing techniques, and nanopore sequencing techniques (e.g., using an Oxford Nanopore technique). Sequencing can additionally or alternatively include methods involving targeted amplicon sequencing and/or metagenomic sequencing. In a specific example of Blocks S130, amplification and sequencing of nucleic acids from biological samples of the set of biological samples includes: solid-phase PCR involving bridge amplification of DNA fragments of the biological samples on a substrate with oligo adapters, wherein amplification involves primers having a forward index sequence (e.g., corresponding to an Illumina forward index for MiSeq/NextSeq/HiSeq platforms), a forward barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, a sequence for targeting a specific target region (e.g., viral target region, 16S rRNA region, 18S rRNA region, ITS region), a reverse index sequence (e.g., corresponding to an Illumina reverse index for MiSeq/NextSeq/HiSeq platforms), and optionally, a reverse barcode sequence. In the specific example, sequencing comprises Illumina sequencing (e.g., with a HiSeq platform, with a MiSeq platform, with a NextSeq platform, etc.) using a sequencing-by-synthesis technique.

Regarding Block S130, some variations of sample processing can include further purification of amplified nucleic acids (e.g., PCR products) prior to sequencing, which functions to remove excess amplification elements (e.g., primers, dNTPs, enzymes, salts, etc.). In examples, additional purification can be facilitated using any one or more of: purification kits, buffers, alcohols, pH indicators, chaotropic salts, nucleic acid binding filters/resins/columns, centrifugation, and any other suitable purification technique.

However, variations of the method 100 can include generating the microbiome sequence dataset S130 in any suitable manner, some embodiments, variations, and examples of which are described in U.S. application Ser. No. 15/097,862, entitled "Method and System for Microbiome-Derived Diagnostics and Therapeutics for Neurological Health Issues", and filed on 13 Apr. 2016, which is herein incorporated in its entirety by this reference.

3.3.A Primer Selection

As shown in FIGS. 1A and 1C, Block S130 can additionally or alternatively include ranking a set of candidate primers according to at least one selected primer feature or target feature S132, which functions to select desired characteristics for one or more primers and/or targets for use in processing a collected sample to generate a microbiome sequence dataset. Ranking a set of candidate primers S132 preferably includes selecting one or more target characteristics (e.g., nucleotide sequence, number of targets, length of target sequences, etc.) and/or primer characteristics (e.g., type, amount, amount in relation to other types of primers, timing and/or stage of when to apply, ranking in relation to other potential primers, etc.) for specifying parameters for potentially processes (e.g., amplification operations, sequencing operations, etc.) associated with generating a microbiome sequence dataset. However, any suitable feature of any suitable component and/or process associated with generating a microbiome sequence dataset can be chosen. Selecting a primer characteristic can include selecting a set of compatible primer types. For example, a selected set of primers can include both viral STD-related primers corresponding to targets associated with the viral STD and the microbiome of the individual, and non-viral STD-related primers corresponding to targets associated with the non-viral STD and the microbiome of the individual. However, any suitable feature can be selected and/or modified for primers and/or targets to be used in generating the microbiome sequence dataset.

With respect to Block S132, ranking a set of candidate primers can be determined (e.g., predetermined, automatically determined, etc.) based on various criteria, including one or more of: desired microbiome information to be presented to a user (e.g., selecting targets based on the information needed to generate a microbiota distribution parameter to be presented in a microbiome analysis to the user, etc.), primer traits (e.g., primer length, primer melting temperature, product melting temperature primer secondary structures, primer annealing temperature, GC content, GC clamp, repeats, runs, 3' end stability, lack of cross homology, lack of template secondary structure, amplicon length, product position, matching of primer pair melting temperature, etc.), specific diseases to diagnose (e.g., selecting primers corresponding to targets correlated with specific disease states), potential treatments for diagnosable diseases (e.g., for an HPV diagnostic kit using user microbiomes, selecting primers for HPV diagnosis and also for assessing efficacy of different HPV treatments), health conditions to assess (e.g., selecting targets for analyzing general health of a collection site of a user), user demographic (e.g., age, ethnicity, geographical locale, etc.), received user responses to surveys (e.g., surveys presented through an application executing on a mobile, a survey included in the sampling kit, an initial screening survey prior to provision of the survey kit, etc.), and/or any other suitable criteria. Such criteria can additionally or alternatively be used in determining fragment size selection, in analyzing for the presence of targets in the generated microbiome sequence dataset, in generating a diagnostic analysis (e.g., for a plurality of STDs, in generating microbiome insights, in generating a therapy recommendation, and/or used for any other suitable portion of the method 100.

Figure 2:
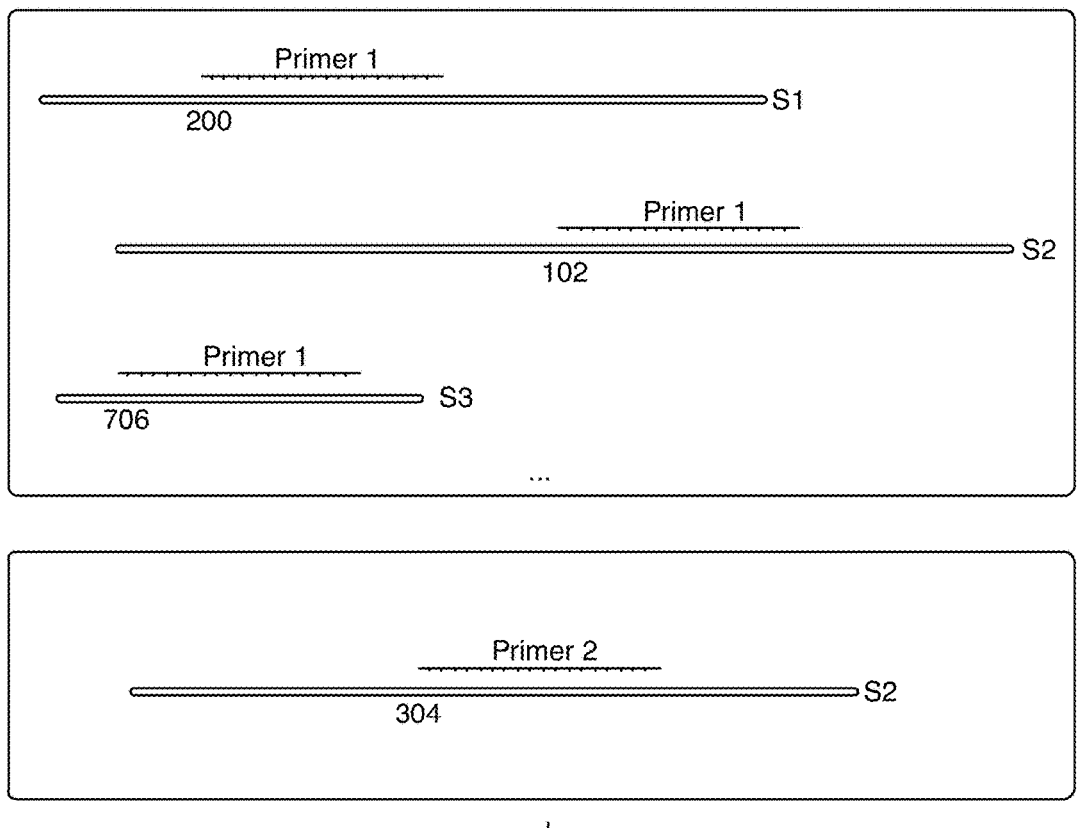
FIG. 2 depicts a variation of a portion of an embodiment of a method for diagnostic testing.

In performing Block S130 with a set of compatible primers, one variation of Block S132 can include implementation of algorithms that index, list, rank, or otherwise identify candidate primers and primer pairs (i.e., forward and reverse primers) according to their ability to generate amplicons from multiple targets (e.g., targets associated with different disease microorganisms). As such, in the example shown in FIG. 2, a first candidate primer/primer pair will be indexed higher if it can amplify sequences of more targets than a second candidate primer/primer pair that can amplify sequences of fewer targets. In this variation, the smallest number of candidate primers/primer pairs that can amplify all targets of the sample associated with the diagnostic test can thus be selected. Additionally or alternatively, another variation of Block S130 can include implementation of algorithms that index, list, rank, or otherwise identify candidate primers and primer pairs (i.e., forward and reverse primers) according to their ability to generate amplicons from sequences of interest (e.g., from prioritized targets associated with diseases of the diagnostic test). As such, in an example, a first candidate primer/primer pair will be indexed higher if it can amplify sequences of more prioritized targets than a second candidate primer/primer pair that can amplify sequences of targets having lower priority. In a specific example, Block S132 can include: ranking a set of potential primers based on ability to generate, from the set of microbiome targets, amplicons associated with the plurality of microorganism types; amplifying, in a multiplexed manner, the nucleic acid content of the microorganism portion of the sample using a set of primers selected based on the ranking; and generating the microbiome sequence dataset from the amplified nucleic acid content. Choosing sets of compatible primers can, however, be implemented in any other suitable manner.

Figure 3:
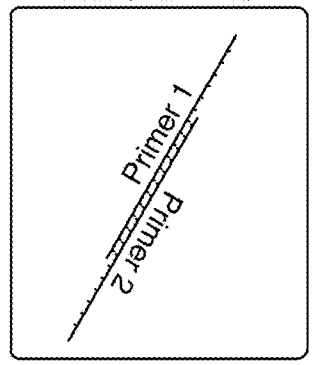
FIG. 3 depicts a variation of a portion of an embodiment of a method for diagnostic testing.
Figure 3:
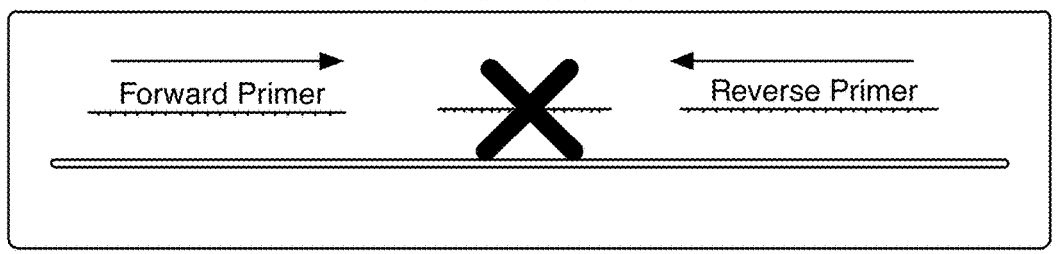

With respect to Block S132, in choosing a set of compatible primers and amplifying targets in the sample contemporaneously or simultaneously (e.g., within a single reaction chamber using the set of compatible primers), the set of primers is preferably selected to avoid inclusion of primers that have beyond a threshold of likelihood to adversely interact (e.g., in forming primer-dimers) with other primers in the set of primers used. Additionally, the set of primers is preferably selected to avoid inclusion of primers that adversely interact with an amplicon, or adversely interfere with amplification performed using another selected primer/primer pair, as shown in the examples of FIG. 3. Selection criteria for the set of compatible primers used in Block S130 can, however, include any other suitable criteria. Furthermore, in some variations wherein adverse interactions are known to occur for different primers of the set of primers used in Block S130, Block S130 can include application of primers of the set of primers in a manner that prevents interference. In one such example, Block S130 can include application of different primers in stages to prevent adverse interactions between primers, and in another example, Block S130 can include use of primers bound to substrates that prevent cross-interactions between primers, as described in U.S. application Ser. No. 14/593, 424 entitled "Method and System for Microbiome Analysis" and filed on 9 Jan. 2015. Prevention of adverse interactions between primers can, however, be mitigated in any other suitable manner.

Block S132 can additionally or alternatively select for primers of the set of primers in limited amounts according to a saturation threshold for each primer, which can prevent or otherwise reduce occurrence of false negative results produced by the diagnostic tests of the method 100. In a specific example, Block S132 can include determining proportional amounts of the viral STD-related primers and the non-viral STD-related primers based on corresponding saturation thresholds and estimated abundances of the corresponding targets in the microorganism portion of the sample. In particular, for samples wherein a first target (e.g., a target associated with human papillomavirus) has high abundance within a sample and a second target (e.g., associated with *chlamydia*) has much lower abundance within the sample, unlimited amounts of different primers used for HPV and *chlamydia* can cause signals associated with HPV to drown out any signals present that are associated with *chlamydia*. As such, using a limited amount of an HPV-related primer can result in HPV primer saturation in a manner that allows *chlamydia*-related targets to be amplified and detected accordingly. As such, anticipated abundance of different targets within a sample can be used to adjust amounts of associated primers used (e.g., in an inverse manner), such that all desired targets can be amplified and detected.

In a variation of Block S132, Block S132 can include manually determining a desired characteristic of a primer and/or target. In this variation, desired features for one or more primers and/or targets can be selected by laboratory personnel (e.g., a professional at the sample handling network, etc.), by a user (e.g., selected in coordination with providing instructions at a sampling kit, etc.), by a care provider (e.g., in accordance with a plurality of STDs that the care provider seeks to test the user for, etc.), and/or by any other suitable individual. However, manually determining a desired characteristic can be performed in any suitable manner.

In another variation of Block S132, Block S132 can include automatically determining a desired characteristic of a primer and/or target. Automatic determination can be based upon models and/or approaches incorporating probabilistic properties, heuristic properties, deterministic properties, and/or any other suitable properties for a identifying, indexing, listing, ranking, and/or selecting parameters for generating a microbiome sequence dataset. However, automatically determining a desired characteristic can be performed in any suitable manner.

Additionally or alternatively, in variations of Block S132, selecting a parameter of a primer and/or target can be performed in a suitable fashion.

3.3.B Amplifying

As shown in FIGS. 1A and 1B, generating a microbiome sequence dataset S130 can additionally or alternatively include: amplifying a set of targets with a set of compatible primers based on selected features for the set of targets and/or the set of compatible primers S134, which functions to process the sample for signal enhancement and/or to provide good limits of detection upon performing sequencing operations. Block S134 can additionally or alternatively function to amplify the nucleic acid targets or nucleic acid tags associated with targets with primers that append sequencing elements to the oligonucleotides in a manner that facilitates sequencing. Amplifying a set of targets is preferably performed according to parameters selected as in Block S132. For example, Block S132 can include selecting types and amounts of primers of a set of primers, and Block S134 can include amplifying the set of targets based on the selected types and amounts of primers. In this example, Block S134 can additionally or alternatively include amplifying the targets using the selected proportional amounts of viral STD-related primers and non-viral STD-related primers. However, amplifying the set of targets can be performed using any suitable parameters. Selected targets designated for amplification can be associated with microorganisms that are unicellular, multicellular, or have any suitable biological composition. In a specific example, Block S134 can include contemporaneously amplifying present targets of a set of targets from the sample with a processing device and a set of compatible primers, wherein the set of targets is associated with both a microbiome of the subject and a set of diseases potentially affecting and/or afflicting the subject. However, the set of targets used in amplification operations can possess any suitable characteristic.

Regarding Block S134, amplification and sequencing of nucleic acids from biological samples of the set of biological samples can include: solid-phase PCR involving bridge amplification of DNA fragments of the biological samples on a substrate with oligo adapters, wherein amplification can involve primers having a forward index sequence (e.g., corresponding to an Illumina forward index for MiSeq/NextSeq/HiSeq platforms) or a reverse index sequence (e.g., corresponding to an Illumina reverse index for MiSeq/NextSeq/HiSeq platforms), a forward barcode sequence or a reverse barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, and a sequence for targeting a specific target region (e.g., 16S rRNA region, 18S rRNA region, ITS region, etc.). Amplification and sequencing can further be performed on any suitable amplicon, as indicated throughout the disclosure. In a specific example, sequencing comprises Illumina sequencing (e.g., with a HiSeq platform, with a MiSeq platform, with a NextSeq platform, etc.) using a sequencing-by-synthesis technique. Additionally or alternatively, any other suitable next generation sequencing technology (e.g., PacBio platform, MinION platform, Oxford Nanopore platform, etc.) can be used. Additionally or alternatively, any other suitable sequencing platform or method can be used (e.g., a Roche 454 Life Sciences platform, a Life Technologies SOLiD platform, etc.). In examples, sequencing can include deep sequencing to quantify the number of copies of a particular sequence in a sample and then also be used to determine the relative abundance of different sequences in a sample. Deep sequencing can refer to highly redundant sequencing of a nucleic acid sequence, for example such that the original number of copies of a sequence in a sample can be determined or estimated. The redundancy (i.e., depth) of the sequencing can be determined by the length of the sequence to be determined (X), the number of sequencing reads (N), and the average read length (L). The redundancy can then be N×L/X. The sequencing depth can be, or be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 110, 120, 130, 150, 200, 300, 500, 500, 700, 1000, 2000, 3000, 4000, 5000 or more. However, amplification and sequencing can be performed in any other suitable manner, and the primers used for amplification can additionally or alternatively have any other suitable functional elements that facilitate downstream processing and analysis according to the method 100.

In variations of Block S134, amplification preferably includes one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. In amplification of purified nucleic acids, the primers used are preferably designed to universally amplify all of the nucleic acid targets in the sample associated with the comprehensive diagnostic test. Additionally or alternatively, the primers can be selected to prevent or minimize amplification bias, as well as configured to amplify nucleic acid regions/sequences (e.g., of a 16S rRNA gene region, an 18S rRNA gene region, the ITS region, etc.) that are informative taxonomically, phylogenetically, for diagnostics, and/or for any other suitable purpose. Thus, universal primers configured to avoid amplification bias can be used in amplification. Primers used in variations of Block S130 can additionally or alternatively include incorporated barcode sequences specific to each sample, which can facilitate identification of biological samples post-amplification. As indicated above, primers used in variations of Block S130 can additionally or alternatively include adaptor regions configured to cooperate with sequencing techniques involving complementary adaptors (e.g., Illumina Sequencing). Additionally or alternatively, primers used in Block S130 can include degenerate primers. Additionally or alternatively, Block S130 can implement any other step configured to facilitate processing (e.g., using a Nextera kit for fragmentation, etc.).

3.3.C Controlling Fragment Size

In some variations, Block S130 can include controlling fragment size selection for amplification, which functions to facilitate a set of fragments covering a desired size range for multiplexed amplification with high specificity and efficiency. In one variation, implementation of Nextera™ technology or other methods of fragmenting nucleic acid sequences can be used to perform a size selection operation to generate amplicons of a desired size or range of sizes. In this variation, adjusting fragmentation process time (or other parameters) can be used to provide fragments of a desired size range for amplification. Additionally or alternatively, in another variation, laboratory methods of size selection (e.g., chromatographic methods, electrophoretic methods, filtration methods, etc.) can be used for size selection to provide fragments of a desired size range for amplification. Size selection can, however, be implemented in any other suitable manner.

In more detail in relation to size selection, quantities of different sizes of fragments can be combined for amplification based upon binding efficiency (e.g., Illumina binding efficiency as a function of fragment length). In particular for a distribution of fragments (e.g., produced using a Nextera™) fragments of different sizes can be combined in a manner that is associated with binding efficiency (e.g., proportional to, inversely proportional to); thus, fragments with low binding efficiency (i.e., long fragments) can have a specified abundance (e.g., lower abundance as proportional to binding efficiency, higher abundance as inversely proportional to binding efficiency) in a sample having a mixture of fragment lengths, and fragments with a high binding efficiency (i.e., shorter fragments) can have a specified abundance (e.g., higher abundance as proportional to binding efficiency, lower abundance as inversely proportional to binding efficiency) in a sample having a mixture of fragment lengths.

Figure 4:
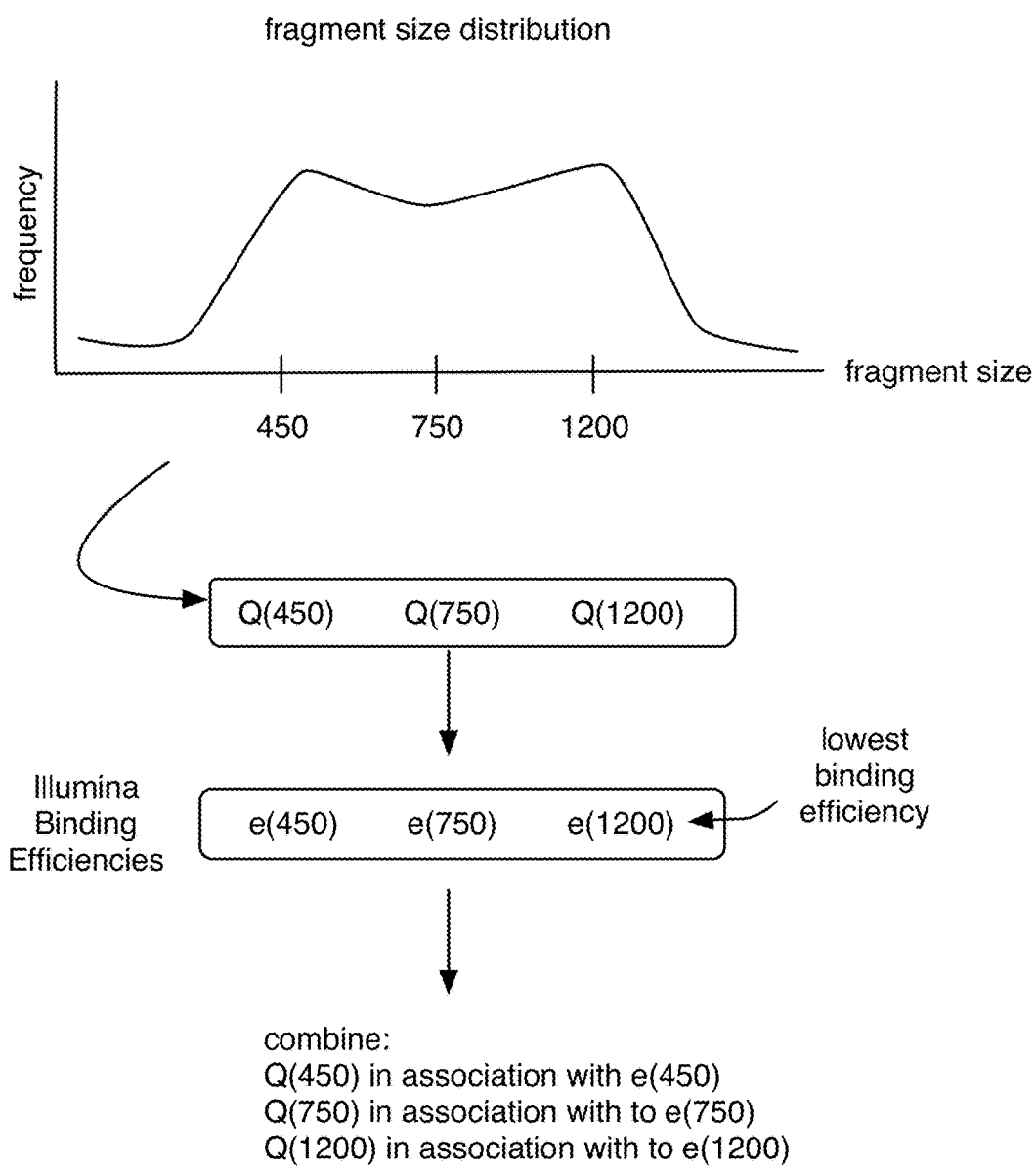
FIG. 4 depicts a specific example of a portion of an embodiment of a method for diagnostic testing.

In the example shown in FIG. 4, for fragment lengths of 450 base pairs (bps), 750 bps, and 1200 bps, with binding efficiencies $e_i(450)$, $e_i(750)$, and $e_i(1200)$, respectively: an abundance of each fragment length, Q(1) can be combined in proportion to $e_i(1)$ to support the amplification process. Fragments of different lengths can, however, be combined in the amplification process in any other suitable manner. In a specific example, Block S130 can include generating the microbiome sequence dataset by processing the nucleic acid content of the papillomavirus microorganisms and the bacterial microorganisms with a fragmentation operation and a multiplexed amplification operation using a set of primers selected for the multiplexed amplification; and selecting a fragment size profile for fragments of the nucleic acid content of the microorganism portion, based on fragment binding efficiency and the selected set of primers, wherein amplifying the nucleic acid content comprises amplifying the nucleic acid content based on the selected fragment size profile. However, incorporating fragment size preferences into generating a microbiome sequence dataset can be performed in any suitable manner.

In any of the above variations and examples, sample processing and amplification of nucleic acids (e.g., nucleic acid fragments) can be performed directly upon microorganism-derived targets (e.g., viral-derived targets, prokaryotic organism-derived targets, eukaryotic organism-derived targets, etc.) from the sample received in Block S120. Additionally or alternatively, sample processing and amplification of nucleic acids (e.g., nucleic acid fragments) can be performed on oligonucleotide tags (e.g., coupled to antibodies that bind to targets of interest from a sample), some variations and examples of which are described in U.S. application Ser. No. 15/183,643 entitled "Method and System for Nucleic Acid Sequencing in Characterization of Antibody Binding Behavior" and filed on 15 Jun. 2016, which is incorporated in its entirety by this reference.

3.4 Detecting Microbiome Targets

As shown in FIGS. 1A-1C, Block S140 recites: detecting a presence of at least one of a set of microbiome targets and a set of targets associated with sexually transmitted diseases (STDs) which functions to assess a microbiome sequence dataset (e.g., generated as in Block S130) for specific features informative of a diagnostic analysis (e.g., as in Block S150) of STDs and/or a therapy recommendation (e.g., as in Block S160). The set of microbiome targets can be associated with, correspond to, and/or be correlated with one or more of a microorganism, a disease state (e.g., an STD, etc.), a panel of diseases (e.g., an STD panel), an individual, a demographic characteristic, a behavioral characteristic, and/or any other suitable entity. Detecting a presence of a set of microbiome targets can include detecting the type, amount, combination, and/or any other suitable properties of one or more microbiome targets. Detecting a presence of a set of microbiome targets can be based on user information, information collected from a group of users (e.g., historical microbiome-related information collected over time through analysis of samples collected across multiple users), information derived from external sources (e.g., the Human Microbiome Project, the Earth Microbiome Project, the Brazilian Microbiome Project), and/or any suitable information. However, the set of microbiome targets can possess any suitable property, and detecting the set of microbiome targets can be based on any suitable criteria.

Regarding Block S140, detecting a presence of a set of microbiome targets is preferably performed at a processing system associated with a sample handling network (e.g., a sample handling network including a processing system), but portions of detecting a set of microbiome targets S140 can additionally or alternatively be performed at any suitable component (e.g., at a user device associated with the user who collects a sample, at a care provider device, etc.) additionally or alternatively be performed at any suitable component.

In relation to Block S140, detecting microbiome targets can be performed in stages (e.g., detecting microbiome targets concurrently with sequencing individual fragments as in Block S130), in aggregate (e.g., after the microbiome sequence dataset has been completely generated for a given collected sample), and/or performed at any suitable time.

Regarding Block S140, identification of target sequences (e.g., associated with a disease panel, associated with the microbiome of the subject) can include mapping of sequence data from sample processing to a subject reference genome (e.g., provided by the Genome Reference Consortium), in order to remove subject genome-derived sequences. Unidentified sequences remaining after mapping of sequence data to the subject reference genome can then be further clustered into operational taxonomic units (OTUs) based upon sequence similarity and/or reference-based approaches (e.g., using VAMPS, using MG-RAST, using QIIME databases), aligned (e.g., using a genome hashing approach, using a Needleman-Wunsch algorithm, using a Smith-Waterman algorithm), and mapped to reference bacterial genomes (e.g., provided by the National Center for Biotechnology Information), using an alignment algorithm (e.g., Basic Local Alignment Search Tool, FPGA accelerated alignment tool, BWT-indexing with BWA, BWT-indexing with SOAP, BWT-indexing with Bowtie, etc.). Mapping of unidentified sequences can additionally or alternatively include mapping to reference archaeal genomes, viral genomes and/or eukaryotic genomes. Furthermore, mapping of taxa can be performed in relation to existing databases, and/or in relation to custom-generated databases. Furthermore, mapping of taxons can be performed in relation to existing databases, and/or in relation to custom-generated databases. Generating the sequence dataset, with alignment, mapping, and assembly, can be performed, at least in part, using an embodiment, variation, or example method described in U.S. application Ser. No. 14/593,424 entitled "Method and System for Microbiome Analysis" and filed on 9 Jan. 2015. However, alignment and mapping can additionally or alternatively be performed in any other suitable manner (e.g., using entropy based approaches).

Figure 5:
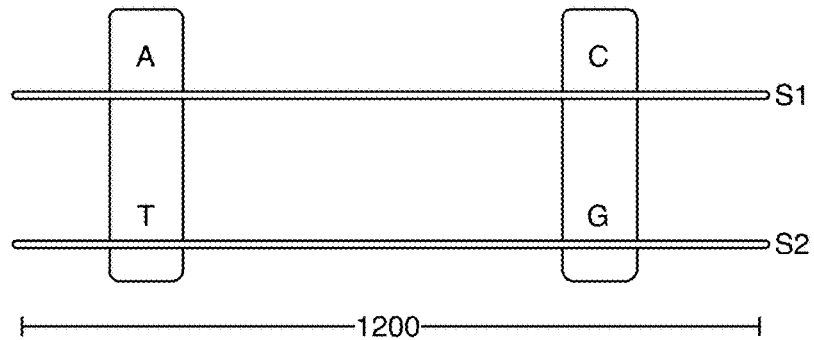
FIG. 5 depicts a specific example of a portion of an embodiment of a method for diagnostic testing.
Figure 5:
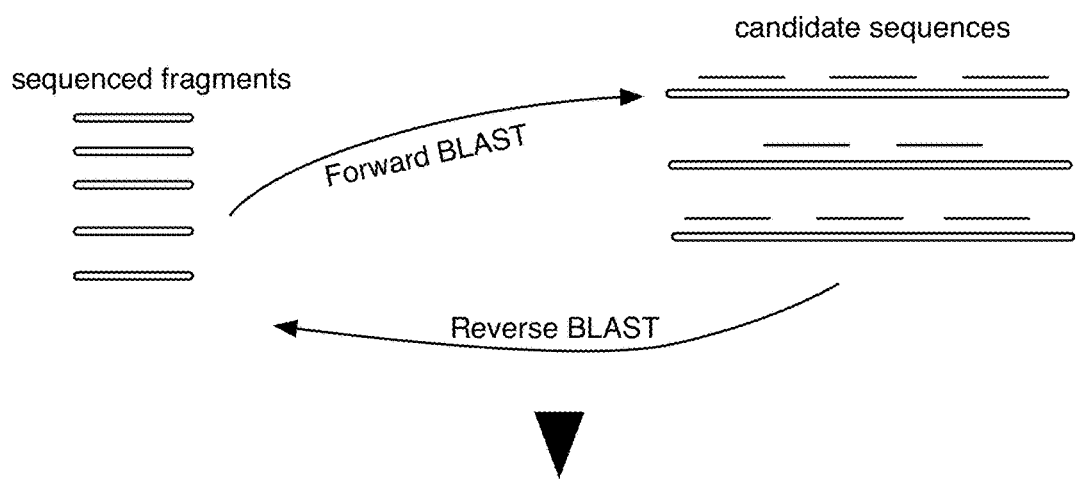

With regard to assembly of sequenced fragments, one variation of Block S150 can implement a forward Basic Local Alignment Search Tool (BLAST) process and a reverse BLAST process, with an entropy-based approach, in order determine an actual assembled sequence from a set of sequenced fragments. In the example shown in FIG. 5, for a set of fragments that have variations in base at one or more regions (but are otherwise identical, as in some polymorphic sequences), a forward BLAST process against a sequence database (e.g., a 16s rRNA database, an 18s rRNA database, a viral database, a custom database, etc.) can provide a candidate set of sequences incorporating sequences of the set of fragments, and a reverse BLAST process of the candidate set of sequences against the set of fragments can be used to determine a distribution of base types (i.e., A, C, T, or G) at each candidate sequence position. An analysis of entropy at each of the sequence positions can thus be used to form sequence clusters, which can be used to determine actual sequences of assembled fragments, as shown in FIG. 5. Assembly can, however, be performed in any other suitable manner, variations and examples of which are described in U.S. application Ser. No. 14/593,424 entitled "Method and System for Microbiome Analysis" and filed on 9 Jan. 2015.

However, detecting a presence of a set of microbiome targets S140 can otherwise be performed in any other suitable manner.

3.5 Generating a Microbiome Functional Diversity Dataset

Block S145 recites: generating a microbiome functional diversity dataset, which functions to create a dataset describing a microbiome functional diversity (e.g., function of microbiota, role of microbiota in physiological structures or processes such as the reproductive system, etc.) of the individual and/or other suitable entity for use in generating a diagnostic analysis as in Block S150 and/or generating a therapy recommendation as in Block S160. A microbiome functional diversity dataset is preferably generated based on a detected set of microbiome targets as in Block S140, but can be generated based on a generated microbiome sequence dataset as in Block S130, and/or any other suitable data from any portion of the method 100.

Regarding Block S145, generating a microbiome functional diversity dataset is preferably performed prior to generating an analysis as in Block S150 and generating a therapy recommendation as in Block S160, but can be performed at any suitable time. Generating a microbiome functional diversity dataset is preferably performed at a processing system used at one or more of Block S150 and/or Block S160, but portions of generating a microbiome functional diversity dataset can be performed at any suitable component.

In relation to Block S145, a microbiome functional diversity dataset can comprise functional features extracted from performing a search of one or more databases, such as the Kyoto Encyclopedia of Genes and Genomes (KEGG) and/or the Clusters of Orthologous Groups (COGs) database managed by the National Center for Biotechnology Information (NCBI). Searching can be performed based upon results of generation of the microbiome composition dataset from one or more of the set of aggregate biological samples and/or sequencing of material from the set of samples. In more detail, Block S145 can include implementation of a data-oriented entry point to a KEGG database including one or more of a KEGG pathway tool, a KEGG BRITE tool, a KEGG module tool, a KEGG ORTHOLOGY (KO) tool, a KEGG genome tool, a KEGG genes tool, a KEGG compound tool, a KEGG glycan tool, a KEGG reaction tool, a KEGG disease tool, a KEGG drug tool, a KEGG medicus tool. Searching can additionally or alternatively be performed according to any other suitable filters. Additionally or alternatively, Block S145 can include implementation of an organism-specific entry point to a KEGG database including a KEGG organisms tool. Additionally or alternatively, Block S145 can include implementation of an analysis tool including one or more of: a KEGG mapper tool that maps KEGG pathway, BRITE, or module data; a KEGG atlas tool for exploring KEGG global maps, a BlastKOALA tool for genome annotation and KEGG mapping, a BLAST/FASTA sequence similarity search tool, and a SIMCOMP chemical structure similarity search tool. In specific examples, Block S145 can include extracting candidate functional features, based on the microbiome composition dataset, from a KEGG database resource and a COG/KOG/POG database or another similar resource; however, Block S145 can comprise extracting functional features in any other suitable manner. For instance, Block S145 can include extracting functional features, including functional features derived from a Gene Ontology functional classification, and/or any other suitable features. Additionally or alternatively, functional features can relate to generation of products that affect environment (e.g., pH, other chemistry, etc.), generation of proteins for specific functions, generation of products in relation to metabolism, and/or any suitable relation to physiological processes of a host. However, generating a microbiome functional diversity dataset S145 can include any elements described in U.S. application Ser. No. 15/097,862 entitled "Method and System for Microbiome-Derived Diagnostics and Therapeutics for Neurological Health Issues" and filed on 13 Apr. 2016, which is hereby incorporated in its entirety by this reference.

3.6 Generating a Diagnostic Analysis

As shown in FIGS. 1A-1C, Block S150 recites: generating a diagnostic analysis based on the detected set of microbiome targets, which functions to analyze sequenced nucleic acid segments/fragments in order to output diagnostic test results pertaining to a disease panel (e.g., an STD panel), and to additionally or alternatively simultaneously characterize a microbiome component (e.g., vaginal flora component, genital microbiota component) of the sample. Block S150 can thereby generate an analysis for providing at least one of the subject and an entity associated with the subject with diagnostic and microbiome information associated with the subject. In a specific example, Block S150 can include: at the processing system and based on the detected set of microbiome targets, generating an analysis informative of (1) diagnostic results for a disease panel (e.g., a plurality of STDs, for a plurality of human papillomavirus types, etc.), and (2) microbiome insights for the individual. However, the analysis generated as in Block S150 can include any suitable information.

In relation to Block S150, portions of generating an analysis can be performed in real-time (e.g., as microbiome targets of a set of microbiome targets are detected as in Block S140, etc.), in response to full completion of a detection operation for a set of microbiome targets, and/or at any suitable time. Generating an analysis can be performed on any portion and/or number microbiome sequence datasets. For example, generating an analysis can be performed on multiple microbiome sequence datasets (e.g., derived from multiple samples) simultaneously, such as through leveraging parallel computing principles, which can thereby improve the efficiency of the processing system. However, different portions of generating the analysis can be performed contemporaneously, simultaneously, in series, in parallel, and/or with any suitable temporal relationship relative each other. Different portions of generating an analysis S150 can be performed at the same processing system (e.g., a processing system used in detecting a set of microbiome targets as in Block S140), at different processing systems (e.g., a processing system at a user device associated with a user collecting a sample with the sampling kit, a remote processing system within the sample handling network, at a remote server, etc.), and/or at any suitable component.

Regarding Block S150, generating an analysis is preferably based at least on the detected set of microbiome targets as in Block S140. Additionally or alternatively, generating an analysis can be derived from, determined by, and/or based on one or more of: a microbiome characteristic dataset (e.g., a microbiome composition dataset, a microbiome functional diversity dataset, etc.) as in Block S170, supplementary data, comparisons of a first microbiome sequence dataset and a second microbiome sequence dataset (e.g., of another individual, a composite microbiome sequence dataset associated with a group of other individuals, a curated microbiome sequence dataset, etc.), information derived from public databases and/or private databases (e.g., a database comprising information collected from a population of users using sampling kits administered as in Block S110, etc.), models (e.g., models incorporating probabilistic properties, heuristic properties, deterministic properties, and/or any other suitable properties), a microbiome functional diversity set (e.g., COG-derived functional features, KEGG-derived functional features, other functional features, etc.), microbiome resilience metrics (e.g., in response to a perturbation determined from a supplementary dataset), abundance of genes that encode proteins or RNAs with given functions (enzymes, transporters, proteins from the immune system, hormones, interference RNAs, etc.), and/or any other suitable component. The generated analysis can include verbal, numerical, graphical, audio, and/or any suitable format of information associated with: disease or a disease panel (e.g., a risk value for a disease in the form of a probability of a positive diagnosis for an STD, etc.), microbiome (e.g., a microbiome insight), behavioral characteristics, demographic characteristics, individual characteristics, population characteristics, and/or any entity characteristic.

However, generating a diagnostic analysis (e.g., based on a microbiome functional diversity dataset) can additionally or alternatively include any elements described in U.S. application Ser. No. 15/097,862 entitled "Method and System for Microbiome-Derived Diagnostics and Therapeutics for Neurological Health Issues" and filed on 13 Apr. 2016, which is hereby incorporated in its entirety by this reference.

In an example, generating an analysis can include: generating a microbiome profile (e.g., profile of collective genomes of microorganisms and/or profile of microorganisms themselves) for the user, and comparing the microbiome profile to a reference microbiome profile. Reference microbiome profiles can include: a "core" microbiome that is shared amongst a community, a healthy reference microbiome profile, an unhealthy reference microbiome profile, a microbiome profile containing markers correlated with a disease state, a panel of diseases (e.g., an STD panel), human reference microbiome profiles, animal reference microbiome profiles, composite microbiome profiles, predetermined microbiome profiles (e.g., manually curated for a specific purpose), automatically determined microbiome profiles (e.g., computer-generated microbiome profiles based on selected criteria), and/or any other suitable reference microbiome profile. Comparisons of microbiome profiles to reference microbiome profiles can be based on the collection site of the microbiome (e.g., taking into account the observation that genital microbiota is dissimilar across individuals, but microbiota at other body regions are more similar across individuals). In a specific example generating a diagnostic analysis for a plurality of STDs can include generating a comparison between the microbiome sequence dataset (e.g., generated as in Block S130 for a collected sample) and a reference microbiome sequence dataset with known correlation to a STD of the plurality of STDs; and generating, for the individual, a positive diagnosis risk value for the STD of the plurality of STDs based on the comparison, wherein presenting information derived from the diagnostic analysis (e.g., as in Block S170) comprises presenting the positive diagnosis risk value.

With respect to generating a diagnostic analysis as in Block S150, diagnostic information is preferably generated for a panel of STD types. Additionally or alternatively, a diagnostic analysis can be generated for any suitable disease state (e.g., non-STDs). Generating a diagnostic analysis preferably includes generating a diagnostic analysis for a panel of STDs including up to a 100 STD types or more, but can additionally or alternatively generated for a panel of any number of STDs and/or other disease states. However, generating diagnostic information indicative of a disease state or panel of disease states can be performed in any other suitable manner.

In relation to Block S150, generating microbiome insights can include generating microbiome-related information indicative of the health of a the collection site of the user (e.g., genital health information associated with the genital microbiome of the subject), a non-collection site, and/or any other suitable site of the user. Additionally or alternatively, microbiome insights can include any one or more of: microbiota distributions (e.g., prokaryotic organism distributions, eukaryotic organism distributions, distributions by taxonomy, distribution by microorganism association with disease state, and/or any other suitable microorganism distribution), microbiome insights regarding any suitable biological structure or process, microbiome insights regarding the collection site in relation to other biological structures or processes (e.g., vaginal microbiome profile compared to overall microbiome profile for a user), general health of the user, insights regarding health of a biological structure microbiome weight (e.g., microbiome weight at the collection site, microbiome weight in relation to an entire organism), microbiome profile, social comparisons (e.g., microbiome profile relative to family members, friends, demographic, sexually active individuals, public at large, specific populations, location, etc.), source of microbiota, and/or any other suitable insights.

In variations of Block S150, insights regarding the source of microbiota identified for a user can include: potential explanations of how a microorganism, microorganism species, and/or microbiota distribution came to share the body space of the user (e.g., environmental factors, physical activity, diet, etc.), when different microbiota began sharing the body space of the user (e.g., in relation to timing of disease transfer, in relation to timing of STD transfer, etc.), where the microbiota are located with respect to the user, and/or any other information associated with microbiota sources. In a specific example, generating an analysis can include: generating confidence metrics or measures of correlational strength between microbiome-based features (or values of parameters derived from features) and behavioral or demographic characteristics derived from the supplementary dataset, and/or any other suitable insights. In the specific example, the behavioral or demographic characteristics can describe a user's characteristics relative other humans in relation to a disease state (e.g., a sexually transmitted infection, HPV, etc.). However, microbiome insights can include any other suitable information.

In a variation of Block S150, generating an analysis can include determining genital microbiome health (e.g., vaginal flora health, etc.) of the user. Assessment of genital microbiome health can include assessing properties of the genital microbiota including: microbiome composition, microbiome functionality (e.g., role of microbiota, input/output of microbiota, interactions with human systems, etc.), environmental properties (e.g., pH, microbiota ecosystem, etc.), and/or any other suitable property. In this variation, the sample collection site is preferably at the genital region of the user, but can be otherwise located. In a specific example, the method 100 can include selecting a set of primers including primers compatible with genital microbiome targets indicative of genital microbiome health, wherein the set of microbiome targets to be detected comprises the genital microbiome targets; generating an analysis indicative of (1) diagnostic results for one or more STDs (e.g., a human papillomavirus type) and (2) microbiome insights for the user, the microbiome insights including a genital microbiome health assessment of the individual; generating a microbiome modification therapy recommendation for improving both (1) the diagnostic results and (2) the genital microbiome health assessment; and presenting the diagnostic results and the genital microbiome health assessment in coordination with presenting the microbiome modification therapy recommendation. However, determining genital microbiome health can be performed in any suitable fashion.

Additionally or alternatively, generating an analysis as in Block S150 can be performed in any other suitable manner.

3.7 Generating a Therapy Recommendation.

As shown in FIGS. 1A-1C, Block 160 recites: generating a therapy recommendation based on the set of microbiome targets S160, which functions to analyze sequenced nucleic acid segments/fragments, microbiome functional features, and/or diagnostic test results in order to provide a treatment suggestion for the individual pertaining to disease (e.g., sexually transmitted diseases), a panel of diseases (e.g., an STD panel), and/or microbial health.

With respect to Block S160, portions of generating a therapy recommendation are preferably performed at a processing system of a sample handling network (e.g., a processing system used in detecting a set of microbiome targets and/or used in generating a diagnostic analysis), but can additionally or alternatively be performed at any suitable component. In relation to temporal aspects of Block S160, generating a therapy recommendation can be performed contemporaneously, simultaneously, in series, in parallel, in coordination with, and/or with any suitable temporal relationship to detecting a set of microbiome targets as in Block S140, generating an analysis as in Block S150, and/or any other portion of the method 100.

Regarding Block S160, generating a therapy recommendation preferably includes generating a therapy recommendation for improving the diagnostic analysis for one or more STDs (e.g., improving diagnostic results for human papillomavirus), but the therapy recommendation can be tailored for any suitable disease state, a panel of diseases (e.g., an STD panel), individual, and/or group of individuals. Types of recommended therapies can include recommendations of consumables, food types, prebiotics, probiotics, phage-based therapies, nutritional supplements, daily habits, physical activities, dietary regimens, medications (e.g., antibiotics, etc.), and/or any other suitable therapy. Additionally or alternatively, therapies can include therapies configured to accentuate or decrease specific functions that would produce an environment that does not promote growth and or spreading of STDs (or other diseases), and/or functions that produce an environment conducive to microbiome health. For example, generating a therapy recommendation can be based on the microbiota functions indicated by a microbiome functional diversity dataset, where the therapy recommendation is configured to alter the microbiota functions, thereby leading to an updated microbiome functional diversity dataset indicating improved microbiota function. In an example, generating a therapy recommendation S160 can include generating a microbiome modification therapy of supplementation with a probiotic. In another example, generating a therapy recommendation S160 can include identifying recommended microorganisms for a user's microbiota profile; and generating a microbiome modification therapy based on the recommended microorganisms. Any number of recommended therapies can be generated for a user, a guardian (e.g., a recommendation for the guardian to encourage the individual to engage in more exercise, etc.), a health professional (e.g., a recommendation for the health professional to prescribe a particular medication based on the user's microbiome composition, etc.), and/or for any suitable entity. However, any suitable therapy recommendation can be generated.

In relation to Block S160, generating a therapy recommendation is preferably based on the detected set of microbiome targets as in Block S140. Additionally or alternatively, generating a therapy can be derived from, determined by, and/or based on one or more of: an analysis (e.g., diagnostic analysis, diagnostic results, microbiome insights, etc.) generated as in Block S150, a microbiome characteristic dataset (e.g., a microbiome composition dataset, a microbiome functional diversity dataset, etc.), public/private databases, supplementary data (e.g., received user responses to surveys, such as surveys presented through an application executing on a mobile computing device, a survey included in the sampling kit, an initial screening survey prior to provision of the survey kit, etc.), user demographic information, a microbiome functional diversity set (e.g., COG-derived functional features, KEGG-derived functional features, other functional features, etc.), microbiome resilience metrics (e.g., in response to a perturbation determined from a supplementary dataset), abundance of genes that encode proteins or RNAs with given functions (enzymes, transporters, proteins from the immune system, hormones, interference RNAs, etc.), and/or any other suitable data (e.g., information used in generating an analysis as in Block S150, etc.). For example, generating a therapy recommendation can be based on modifying microbiome composition and/or functional diversity features derived from a microbiome characteristic dataset, in order to foster a microbiome environment conducive to treating a disease state. In a specific example, the method 100 can include: at the processing system and based on the detected set of microbiome targets, generating a microbiome functional diversity dataset describing a microbiome functional diversity of the individual, wherein generating the analysis and generating the microbiome modification therapy recommendation are further based on the microbiome functional diversity dataset. In this specific example, the microbiome composition dataset can include indicators of a composition of the plurality of microorganism types associated with a plurality of STDs, wherein the microbiome functional diversity dataset can include indicators of microbiome functions associated with a STD of the plurality of STDs, and wherein the therapy recommendation prompts a microbiome modification therapy configured to modify (1) the composition of the plurality of microorganism types, and (2) the microbiome functions associated with the STD. Additionally or alternatively, in the specific example, the microbiome functional diversity dataset can include indicators of microbiome functions associated with human papillomavirus, and the microbiome modification therapy recommendation can prompt a human papillomavirus therapy configured to modify the microbiome functions associated with human papillomavirus. However, a therapy recommendation can be generated from any suitable information.

In a variation of Block S160, generating a therapy recommendation can include enabling a health professional to generate the therapy recommendation. In this variation, a microbiome sequence dataset and/or information regarding a detected set of microbiome targets at a microbiome sequence dataset can be presented to a health professional (e.g., a physician, a dietician, a researcher, a microbiota expert, etc.) for review and analysis in generating a therapy recommendation for the user. Enabling the health professional to generate the therapy recommendation can include guiding the health professional through generation of a therapy recommendation (e.g., by highlighting relevant properties of the detected set of microbiome targets). However, enabling one or more health professionals to generate the therapy recommendation can be performed in any suitable manner.

Figure 7:
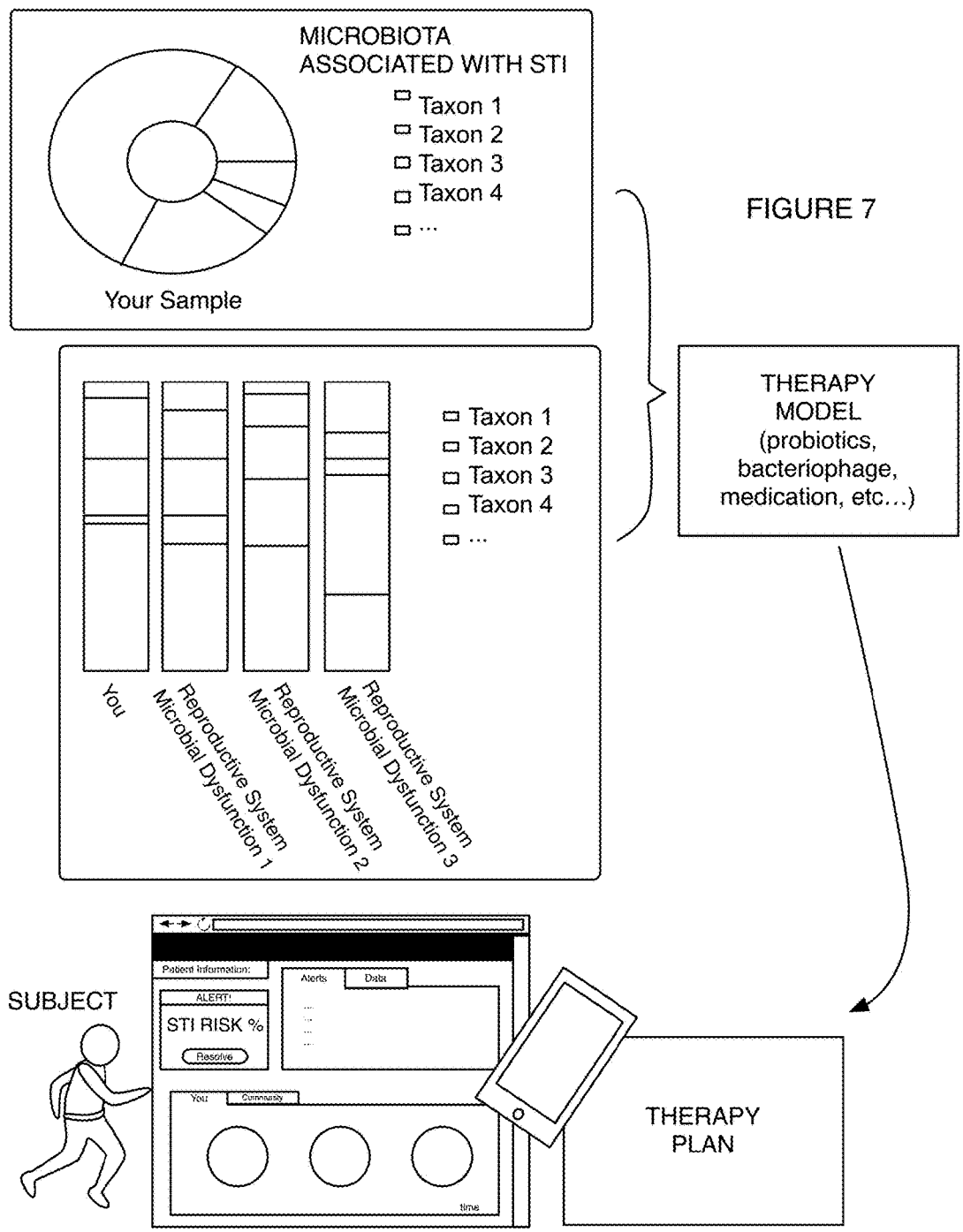
FIG. 7 depicts a specific example of a portion of an embodiment of a method for diagnostic testing.

As shown in FIG. 7, in another variation of Block S160, generating a therapy recommendation can include automatically generating a therapy recommendation (e.g., using one or more therapy recommendation models possessing probabilistic properties, heuristic properties, deterministic properties, and/or any other suitable properties, etc.). For example, therapy recommendations can be generated using a machine learning classifier with features derived from a microbiome sequenced dataset, a detected set of microbiome targets, a diagnostic analysis, user survey responses, and/or any suitable information. In a specific example, generating a therapy recommendation can be based on a microbiome composition dataset and a microbiome functional diversity dataset (e.g., derived from assessing the detected set of microbiome targets), where generating the therapy recommendation can include extracting microbiome features from at least one of the microbiome composition dataset and the microbiome functional diversity dataset, generating the therapy recommendation using the extracted microbiome features with a machine learning model trained upon a microbiome feature training set associated with a group of other individuals, wherein the microbiome features and the training set microbiome features share at least one microbiome feature type. However, automatically generating a therapy recommendation can be performed in any other suitable manner.

Additionally or alternatively, generating a therapy recommendation can be performed in any suitable fashion.

3.8 Outputting Information.

As shown in FIGS. 1A-1C, Block S170 recites: promoting the therapy recommendation in coordination with presenting information derived from the diagnostic analysis, which functions to relate information associated with at least one of the diagnostic analysis (e.g., generated in S150) and the therapy recommendation (e.g., generated in S160) to the user and/or other suitable entities. Promoting the therapy recommendation (e.g., the therapy recommendation generated in Block S160) can be performed contemporaneously, simultaneously, in series, in parallel, and/or with any suitable temporal relationship relative presenting information related to the analysis generated in Block S150. However, any portion of outputting information S170 can be performed at any suitable time.

Figure 6:
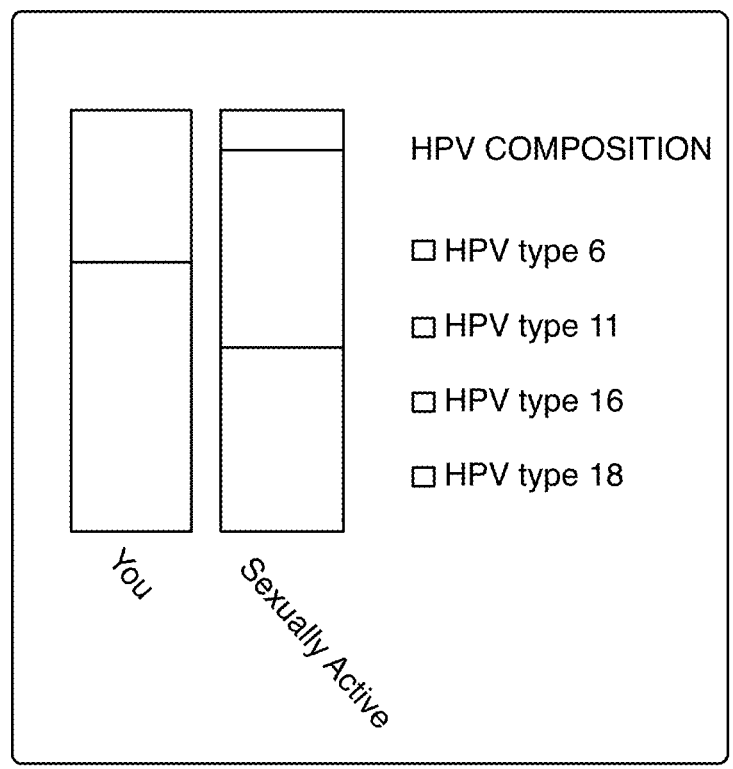
FIG. 6 depicts a specific example of a portion of an embodiment of a method for diagnostic testing.

As shown in FIGS. 6-7, regarding Block S170, outputted information be represented in any number or combination of forms, including numerical (e.g., composition characterizations of microbiota, risk values for disease panels, probabilities, raw values, processed values, etc.), verbal (e.g., verbal warnings, alerts, recommendations, risk levels, etc.), graphical (e.g., colors indicating risk state, educational graphics, diagrams explaining microbiome correlations with different STDs and/or characteristics, etc.), and/or any suitable form. Outputted information relating to disease can include: prevalence information (e.g., prevalence of HPV in a given population), social comparison information (e.g., comparison with individuals in a similar demographic profile regarding characteristics related to the disease), risk information, symptom information, treatment information, and/or any other suitable information related to an analyzed disease state. However, Block S170 can output any suitable information related to Blocks S150, S160, and/or any other portion of the method 100.

In relation to Block S170, one or more components of the sample handling network (e.g., a processing system, a communications module, etc.) preferably transmit the microbiome-related information to a user device of the user (e.g., at a web interface, an application executing on a mobile device of the user, etc.) and/or other suitable entity (e.g., a guardian, a health professional, etc.). However, any suitable component can transmit, receive, and/or present any suitable information to any suitable entity.

With respect to Block S170, outputting information can include outputting the information for the user based on rules (e.g., notification preferences set by a user, rules established by a care provider, by a guardian, etc.), time (e.g., notification at set frequencies, times of day, etc.), steps (e.g., outputting information derived from the analysis generated in Block S150 in response to generating the analysis; outputting the therapy recommendation generated in Block S160 in response to generating the therapy recommendation, etc.), and/or any other suitable criteria.

Regarding Block S170, a specific example can include: based on the detected set of microbiome targets and/or microbiome functional features, generating an analysis comprising microbiome insights including a sample distribution of taxonomic groups of microorganisms present in the sample and/or functions of the microbiome; presenting information derived from the analysis, comprising presenting a first graphic depicting the sample distribution of taxonomic groups of microorganisms present in the sample compared to a distribution for a group of other individuals. In this specific example, the sample distribution can include a proportion of the plurality of papillomavirus types, and wherein the first graphic depicts the proportion of the plurality of papillomavirus types compared to a proportion of the plurality of papillomavirus types for a group of other individuals. Additionally or alternatively, the specific example can include promoting a microbiome modification therapy, comprising presenting a second graphic depicting efficacy of the microbiome modification therapy recommendation for a group of other individuals, in coordination with presenting the first graphic. However, Block S170 can be otherwise performed in any other suitable manner.

3.8.A Presenting Information Derived from a Diagnostic Analysis

Block S170 can include presenting information derived from the diagnostic analysis S172, which functions to communicate information associated with the analysis generated in Block S160 to the user. The outputted information preferably indicates a positive, a negative, and/or an inconclusive test result for each of a set of diseases of interest, based upon the assembled and mapped sequences of the sequence dataset. The output of the analysis preferably also characterizes collection site-related microbiome information of the subject.

Regarding Block S170, in a specific application for STD and genital microbiome testing, the output of the analysis can provide positive, negative, and inconclusive test results associated with: high risk and other Papillomavirus types (e.g., Human papillomavirus types 1a, 2, 2a, 3, 4, 5, 5b, 6, 6a, 6b, 7, 8, 9, 10, 11, 12, 13, 14D, 15, 16, 17, 18, 19, 20, 21, 22, 23, 24, 25, 26, 27, 27b, 28, 29, 30, 31, 32, 33, 34, 35, 36, 37, 38, 38b, 39, 40, 41, 43, 44, 45, 47, 48, 49, 50, 51, 52, 53, 55, 56, 57, 57b, 58, 59, 60, 61, 62, 63, 65, 66, 67, 68, 68a, 68b, 69, 70, 71, 72b, 78, 81, 82, 83, 84, 86, 87, 88, 90, 94, 97, 98, 99, 100, 101, 102, 103, 104, 105, 106, 107, 108, 109, 110, 111, 112, 113, 114, 115, 117, 118, 119, 120, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 154, 155, 156, 159, 163, 171, 172, 173 and 197), Herpes simplex virus (Herpes simplex virus types 1 and 2), human immunodeficiency virus (HIV, types I and II), Chancroid, *Chlamydia, Gonorrhea, Mycoplasma*, Vaginitis, Syphilis, and Trichomoniasis.

Regarding Block S170, in relation presenting information related to microbiome insights (e.g., insights generated as in Block S150), the output of the analysis of can provide characterization of prokaryotic organism distributions, eukaryotic organism distributions, other suitable microorganism distribution information (e.g., associated with the genital microbiome of the subject), and/or any other suitable microbiome insight information. Correlations between the diagnostic test of the subject and microbiome insights can further be generated and provided in the analysis of Block S150, for instance, according to methods described in U.S. application Ser. No. 14/593,424 entitled "Method and System for Microbiome Analysis" and filed on 9 Jan. 2015. However, presenting information based on the diagnostic analysis S172 can be performed in any suitable manner.

3.8.B Promoting a Therapy Recommendation

Block S170 can include promoting a therapy recommendation S172, which functions to communicate and/or facilitate a treatment suggestion (e.g., a therapy recommendation generated in Block S160) for the user. Promoting a therapy recommendation preferably includes presenting the therapy recommendation to the user at a user device associated with the user. Additionally or alternatively, promoting the therapy recommendation can include automatically implementing a portion of the therapy suggestion or the entire therapy recommendation. For example, if the therapy recommendation is to talk with a healthcare professional about diagnostic results generated as in Block S150, automatically implementing the therapy suggestion can include automatically facilitating communication with a care provider (e.g., through telemedicine, digital communications, automatically scheduling a physician appointment, etc.). In another example, automatically implementing a portion of the therapy suggestion can include transmitting the therapy recommendation to a care provider (e.g., if risk factors for an STD of a panel of STDs exceed a threshold), but any suitable information can be transmitted to a third party. However, promoting a therapy recommendation can be performed in any suitable fashion.

Additionally or alternatively, outputting information can include any embodiment, variation, or example of outputting information, as described in U.S. application Ser. No. 14/919,614 entitled "Method and System for Microbiome-Derived Diagnostics and Therapeutics" and filed on 21 Oct. 2015, which is hereby incorporated in its entirety by this reference. However, outputting information S170 can be performed in any suitable fashion.

The method 100 can, however, include any other suitable blocks or steps configured to facilitate reception of biological samples from subjects, processing of biological samples from subjects, analyzing data derived from biological samples, and generating diagnostic tests from samples from the subjects. For instance, the method 100 can further include generation of and/or output of a confidence metric associated with a diagnostic result and/or a characterization of the microbiome of the subject.

4. System.

As shown in FIG. 1B, an embodiment of a system 200 for providing disease diagnosis through analysis of a microbiome of an individual can include: a sample handling network (e.g., with sample kit distribution and sample reception modules); a sample processing module, in communication with the sample handling network, that amplifies targets of received samples and generates sequence datasets associated with targets of the samples; and a processing system configured to generate and provide analyses derived from processing of the samples, in support of diagnostic tests of the received samples.

The system 200 functions to comprehensively analyze a received sample for providing diagnostic results (e.g., regarding a plurality of STDs) and/or tailored therapy recommendations to an individual based on their microbiome.

In some embodiments, the system 200 and/or components of the system 200 can additionally or alternatively include or communicate data to and/or from: a user database (storing user account information, user microbiome information, user profiles, user health records, user demographic information, associated care provider information, associated guardian information, user device information, etc.), an analysis database (storing computational models, collected data, historical data, public data, simulated data, generated datasets, generated analyses, diagnostic results, therapy recommendations, etc.), and/or any other suitable computing system.

Database(s) and/or portions of the method 100 can be entirely or partially executed, run, hosted, or otherwise performed by: a remote computing system (e.g., a server, at least one networked computing system, stateless computing system, stateful computing system, etc.), a user device (e.g., a device of a user executing an application for analyzing microbiome samples and/or sequenced microbiome datasets, etc.), a care provider device (e.g., a device of a care provider associated with a user), a machine configured to receive a computer-readable medium storing computer-readable instructions, or by any other suitable computing system possessing any suitable component (e.g., a graphics processing unit, a communications module, etc.). However, the modules of the system 200 can be distributed across machine and cloud-based computing systems in any other suitable manner.

Devices implementing at least a portion of the method 100 can include one or more of: a smartwatch, smartphone, a wearable computing device (e.g., head-mounted wearable computing device), tablet, desktop, a supplemental sensor, a biosignal detector, a medical device, and/or any other suitable device. All or portions of the method 100 can be performed by one or more of: a native application, web application, firmware on the device, plug-in, and any other suitable software executing on a device. Device components used with the method 100 can include an input (e.g., keyboard, touchscreen, etc.), an output (e.g., a display), a processor, a transceiver, and/or any other suitable component, wherein data from the input device(s) and/or output device(s) can be generated, analyzed, and/or transmitted to entities for consumption (e.g., for a user to assess their diagnostic results, microbiome insights, and/or therapy recommendations.) Communication between devices and/or databases can include wireless communication (e.g., WiFi, Bluetooth, radiofrequency, etc.) and/or wired communication.

Components of the sample handling network (e.g., a processing system) and/or any other suitable component of the system 200, and/or any suitable step of the method 100 can employ machine learning approaches including any one or more of: supervised learning (e.g., using logistic regression, using back propagation neural networks, using random forests, decision trees, etc.), unsupervised learning (e.g., using an Apriori algorithm, using K-means clustering), semi-supervised learning, reinforcement learning (e.g., using a Q-learning algorithm, using temporal difference learning), and any other suitable learning style. Each module of the plurality can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial least squares regression, Sammon mapping, multidimensional scaling, projection pursuit, etc.), an ensemble method (e.g., boosting, bootstrapped aggregation, AdaBoost, stacked generalization, gradient boosting machine method, random forest method, etc.), and any suitable form of machine learning algorithm. Each processing portion of the method 100 can additionally or alternatively leverage: a probabilistic module, heuristic module, deterministic module, or any other suitable module leveraging any other suitable computation method, machine learning method or combination thereof.

In relation to the sample handling network, the network can function to receive, process, and analyze a collected sample to generate and distribute diagnostic results (e.g., for an STD), microbiome insights, and/or a therapy recommendation for a user based on detected microbiome targets of a sequenced microbiome dataset. The sample handling network can additionally or alternatively function to provide a sample kit to a user (e.g., in response to a purchase order for a sample kit). The sample handling network is preferably remote from a user, such that a user can conveniently send a collected sample to the sample handling network, and subsequently digitally receive results based on the collected sample. Additionally or alternatively, the sample handling network can include user action (e.g., a user pre-processing a sample), a user device (e.g., an application executing on a mobile device that aids in the analysis of the sample), a remote server, and/or any other suitable entity. However, the sample handling network can be configured in any suitable manner.

In relation to the sample processing module, the module can function to process a collected sample into a form suitable for sequencing and/or analysis in generating diagnostic results, microbiome insights, and/or a recommended therapy. The sample processing module can facilitate manual performance of processing steps (e.g., facilitating lab technicians in performing processing steps on collected samples) and/or automatic performance of processing steps (e.g., using automated devices in generating processed samples). However, the sample processing module can be configured in any suitable manner.

In relation to the processing system, the processing system can function to analyze a processed sample (e.g., a microbiome sequence dataset) for the presence of a set of microbiome targets in order to infer information regarding a diagnostic analysis, microbiome insights, and/or a recommended therapy. However, the processing system can be configured in any suitable manner.

The method 100 and/or system 200 of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the embodiments of the invention without departing from the scope of this invention as defined in the following claims.

We claim:

1. A method for characterizing human papillomavirus contemporaneously with generating analysis of a microbiome of an individual, comprising:
   from a sample handling network, providing a sampling kit to the individual at a location remote from the sample handling network, the sampling kit including a sample container configured to receive a sample from a collection site of the individual;
   at the sample handling network, receiving the sample container with the sample collected from the collection site of the individual;
   at a sample processing module within the sample handling network, generating a microbiome composition dataset based upon sequencing nucleic acid content of a microorganism portion of the sample;
   detecting a presence of a set of microbiome targets at the microbiome composition dataset, the set of microbiome targets associated with both: (1) a plurality of human papillomavirus types and (2) the microbiome of the individual;
   generating a microbiome functional diversity dataset based on the detected set of microbiome targets;
   generating an analysis informative of both: (1) diagnostic results for human papillomavirus, and (2) microbiome insights for the individual, based on the detected set of microbiome targets and the microbiome functional diversity dataset;
   determining a microbiome modification therapy for improving health of the individual with human papillomavirus, based on the detected set of targets, the diagnostic results for human papillomavirus, and the microbiome functional diversity dataset; and
   providing, to the individual at a user device associated with the individual, the microbiome modification therapy in coordination with presenting information derived from the analysis.

2. The method of claim 1, wherein the microbiome functional diversity dataset comprises indicators of microbiome functions associated with a panel of sexually transmitted diseases, and wherein the microbiome modification therapy prompts a therapy configured to modify the microbiome functions associated with the panel of sexually transmitted diseases.

3. The method of claim 2, wherein the panel of sexually transmitted diseases comprises human papillomavirus, wherein the microbiome functional diversity dataset comprises indicators of microbiome functions associated with human papillomavirus, and wherein the therapy modifies the microbiome functions associated with human papillomavirus.

4. The method of claim 1, wherein the microbiome insights comprise a sample distribution of taxonomic groups of microorganisms present in the sample, and wherein presenting information derived from the analysis comprises presenting a first graphic depicting the sample distribution of taxonomic groups of microorganisms present in the sample compared to a distribution for a group of other individuals.

5. The method of claim 4, wherein the sample distribution comprises a proportion of the plurality of human papillomavirus types, and wherein the first graphic depicts the proportion of the plurality of human papillomavirus types compared to a proportion of the plurality of human papillomavirus types for a group of other individuals.

6. The method of claim 5, wherein providing the microbiome modification therapy comprises presenting a second graphic depicting efficacy of the microbiome modification therapy for a group of other individuals, in coordination with presenting the first graphic.

7. The method of claim 1, wherein the microorganism portion comprises human papillomavirus microorganisms and other microorganisms, and wherein generating the microbiome composition dataset comprises generating the microbiome composition dataset based upon sequencing nucleic acid content of the human papillomavirus microorganisms and other microorganisms.

8. The method of claim 7, wherein generating the microbiome composition dataset comprises processing the nucleic acid content of the human papillomavirus microorganisms and the other microorganisms with a fragmentation operation and a multiplexed amplification operation using a set of primers selected for the multiplexed amplification operation.

9. The method of claim 8, wherein the selected set of primers comprises primers compatible with genital microbiome targets indicative of genital microbiome health, wherein the set of microbiome targets comprises the genital microbiome targets, wherein the microbiome insights comprise a genital microbiome health assessment of the individual, wherein determining the microbiome modification therapy comprises determining the microbiome modification therapy for improving both: (1) health of the individual with human papillomavirus and (2) the genital microbiome health assessment, and wherein presenting the information derived from the analysis comprises presenting the genital microbiome health assessment in coordination with presenting the microbiome modification therapy.

* * * * *